(12) United States Patent
Chen et al.

(10) Patent No.: US 11,685,743 B2
(45) Date of Patent: Jun. 27, 2023

(54) OPEN-SHELL PI-CONJUGATED MOLECULES EXHIBITING MULTIDIMENSIONAL INTERMOLECULAR COVALENCY, COMPOSITIONS AND PROCESS FOR PREPARING

(71) Applicant: Lehigh University, Bethlehem, PA (US)

(72) Inventors: Mark Chen, Bethlehem, PA (US); Caleb Wehrmann, Bethlehem, PA (US); Ryan Charlton, Collegeville, PA (US)

(73) Assignee: Lehigh University

( * ) Notice: Subject to any disclaimer, the term of this patent is extended or adjusted under 35 U.S.C. 154(b) by 4 days.

(21) Appl. No.: 17/057,488

(22) PCT Filed: May 21, 2019

(86) PCT No.: PCT/US2019/033361
§ 371 (c)(1),
(2) Date: Nov. 20, 2020

(87) PCT Pub. No.: WO2019/226678
PCT Pub. Date: Nov. 28, 2019

(65) Prior Publication Data
US 2021/0363153 A1     Nov. 25, 2021

Related U.S. Application Data

(60) Provisional application No. 62/674,480, filed on May 21, 2018.

(51) Int. Cl.
*C07D 493/06* (2006.01)
*C07D 471/06* (2006.01)

(52) U.S. Cl.
CPC ......... *C07D 493/06* (2013.01); *C07D 471/06* (2013.01)

(58) Field of Classification Search
CPC ............................ C07D 471/06; C07D 493/06
See application file for complete search history.

(56) References Cited

U.S. PATENT DOCUMENTS

2012/0273764 A1   11/2012   Yu et al.
2013/0153874 A1   6/2013   Kato

FOREIGN PATENT DOCUMENTS

WO   WO 2018/039347    3/2018

OTHER PUBLICATIONS https://pubs.acs.org/doi/full/10.1021/jacs.8b13300.
https://chemistry-europe.onlinelibrary.wiley.com/doi/abs/10.1002/chem.201706002.

*Primary Examiner* — Susanna Moore
(74) *Attorney, Agent, or Firm* — The Belles Group, P.C.

(57) ABSTRACT

Disclosed herein are compound capable of exploiting non-bonding electron densities, for example, cationic open-shell, pi-conjugated bisphenalenyls wherein intermolecular covalent bonding interactions can occur in multiple dimensions. Further disclosed are compositions comprising the disclosed compounds and process for the preparation thereof.

12 Claims, 12 Drawing Sheets

OPEN-SHELL PI-CONJUGATED MOLECULES EXHIBITING MULTIDIMENSIONAL INTERMOLECULAR COVALENCY, COMPOSITIONS AND PROCESS FOR PREPARING

CROSS-REFERENCE TO RELATED PATENT APPLICATION

The present application is a national stage entry under 35 U.S.C. § 371 of International Patent Application No. PCT/US2019/033361, which claims the benefit of priority from U.S. Provisional Patent Application No. 62/674,480, filed May 21, 2018, the contents of which are hereby incorporated herein in their entireties.

FIELD OF THE DESCRIPTION

Disclosed herein are compounds capable of exploiting non-bonding electron densities, for example, cationic open-shell, pi-conjugated bisphenalenyls wherein intermolecular covalent bonding interactions can occur in multiple dimensions. Further disclosed are compositions comprising the disclosed compounds and process for the preparation thereof.

DETAILED DESCRIPTION

Figure 1:
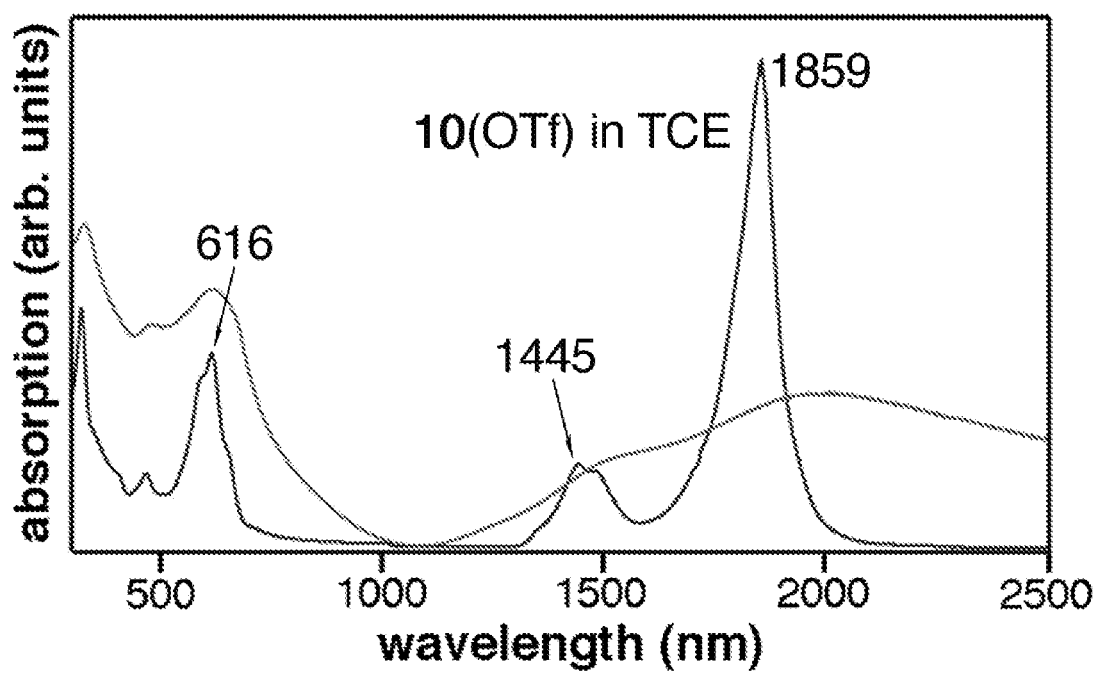
FIG. 1 is the UV-visible-NIR spectrum of compound 7 in 1,1,2,2-tetrachloroethane (TCE) solution and as a thin film.

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (o C) unless otherwise specified.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill.

The term "hydrocarbyl" refers to any moiety or substitution on a moiety that comprises carbon and hydrogen. Hydrocarbyl units can comprise one or more heteroatoms such as oxygen, nitrogen, sulfur and the like.

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted "alkoxy" are used herein denotes a unit having the general formula —$OR^{100}$ wherein $R^{100}$ is an alkyl unit as defined herein above, for example, methoxy, methoxymethyl, methoxymethyl.

The term "aryl" as used herein denotes cyclic organic units that comprise at least one benzene ring having a conjugated and aromatic six-membered ring, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term "heteroaryl" denotes an organic unit comprising a five or six membered conjugated and aromatic ring wherein at least one of the ring atoms is a heteroatom selected from nitrogen, oxygen, or sulfur. The heteroaryl rings can comprise a single ring, for example, a ring having 5 or 6 atoms wherein at least one ring atom is a heteroatom not limited to nitrogen, oxygen, or sulfur, such as a pyridine ring, a furan ring, or thiofuran ring. A "heteroaryl" can also be a fused multicyclic and heteroaromatic ring system having wherein at least one of the rings is an aromatic ring and at least one atom of the aromatic ring is a heteroatom including nitrogen, oxygen, or sulfur.

The following are non-limiting examples of heteroaryl rings according to the present disclosure:

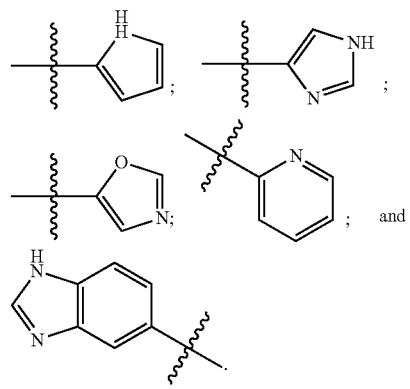

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

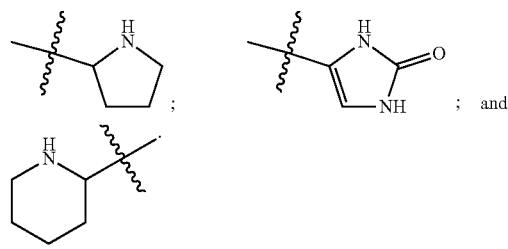

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

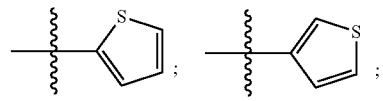 [SMILES: *c1cccs1 ; *c1ccsc1]

whereas in naming the compounds of the present disclosure, the chemical nomenclature for these moieties are typically spelled "thiophen-2-yl and thiophen-3-yl" respectively.

Herein the terms "thiophene-2-yl and thiophene-3-yl" are used when describing these rings as units or moieties which make up the compounds of the present disclosure solely to make it unambiguous to the artisan of ordinary skill which rings are referred to herein.

The following are non-limiting examples of units which can substitute for hydrogen atoms on R, $R^1$, $R^2$, $R^4$, $R^5$, $R^6$, $R^7$ or other unit:

i) linear, branched, or cyclic alkyl, alkenyl, and alkynyl; for example, methyl ($C_1$), ethyl ($C_2$), n-propyl ($C_3$), iso-propyl ($C_3$), cyclopropyl ($C_3$), propylen-2-yl ($C_3$), propargyl ($C_3$), n-butyl ($C_4$), iso-butyl ($C_4$), sec-butyl ($C_4$), tert-butyl ($C_4$), cyclobutyl ($C_4$), n-pentyl ($C_5$), cyclopentyl ($C_5$), n-hexyl ($C_6$), and cyclohexyl ($C_6$);

ii) substituted or unsubstituted aryl; for example, phenyl, 2-fluorophenyl, 3-chlorophenyl, 4-methylphenyl, 2-aminophenyl, 3-hydroxyphenyl, 4-trifluoromethylphenyl, and biphenyl-4-yl;

iii) substituted or unsubstituted heterocyclic;

iv) substituted or unsubstituted heteroaryl;

v) $-(CR^{12a}R^{12b})_qOR^{11}$; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;

vi) $-(CR^{12a}R^{12b})_qC(O)R^{11}$; for example, $-COCH_3$, $-CH_2COCH_3$, $-OCH_2CH_3$, $-CH_2COCH_2CH_3$, $-COCH_2CH_2CH_3$, and $-CH_2COCH_2CH_2CH_3$;

vii) $-(CR^{12a}R^{12b})_qC(O)OR^{11}$; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;

viii) $-(CR^{12a}R^{12b})_qC(O)N(R^{11})_2$; for example, $-CONH_2$, $-CH_2CONH_2$, $-CONHCH_3$, $-CH_2CONHCH_3$, $-CON(CH_3)_2$, and $-CH_2CON(CH_3)_2$;

ix) $-(CR^{12a}R^{12b})_qOC(O)N(R^{11})_2$; for example, $-OC(O)NH_2$, $-CH_2OC(O)NH_2$, $-OC(O)NHCH_3$, $-CH_2OC(O)NHCH_3$, $-OC(O)N(CH_3)_2$, and $-CH_2OC(O)N(CH_3)_2$;

x) $-(CR^{12a}R^{12b})_qN(R^{11})_2$; for example, $-NH_2$, $-CH_2NH_2$, $-NHCH_3$, $-N(CH_3)_2$, $-NH(CH_2CH_3)$, $-CH_2NHCH_3$, $-CH_2N(CH_3)_2$, and $-CH_2NH(CH_2CH_3)$;

xi) halogen: $-F$, $-Cl$, $-Br$, and $-I$;

xii) $-CH_mX_n$; wherein X is halogen, m is from 0 to 2, m+n=3; for example, $-CH_2F$, $-CHF_2$, $-CF_3$, $-CCl_3$, or $-CBr_3$;

xiii) $-(CR^{12a}R^{12b})_qCN$; for example; $-CN$, $-CH_2CN$, and $-CH_2CH_2CN$;

xiv) $-(CR^{12a}R^{12b})_qNO_2$; for example; $-NO_2$, $-CH_2NO_2$, and $-CH_2CH_2NO_2$;

xv) $-(CR^{12a}R^{12b})_qSO_2R^{11}$; for example, $-SO_2H$, $-CH_2SO_2H$, $-SO_2CH_3$, $-CH_2SO_2CH_3$, $-SO_2C_6H_5$, and $-CH_2SO_2C_6H_5$; and xvi) $-(CR^{12a}R^{12b})_qSO_3R^{11}$; for example, $-SO_3H$, $-CH_2SO_3H$, $-SO_3CH_3$, $-CH_2SO_3CH_3$, $-SO_3C_6H_5$, and $-CH_2SO_3C_6H_5$;

xvii) hydroxyl groups or thiol groups, xviii) amino groups, monosubstituted amino, or disubstituted amino, wherein each $R^{11}$ is independently hydrogen, substituted or unsubstituted $C_1$-$C_4$ linear, branched, or cyclic alkyl; or two $R^{11}$ units can be taken together to form a ring comprising 3-7 atoms; $R^{12a}$ and $R^{12b}$ are each independently hydrogen or $C_1$-$C_4$ linear or branched alkyl; the index q is from 0 to 4.

Disclosed herein are compound capable of exploiting non-bonding electron densities, for example, cationic open-shell, pi-conjugated bisphenalenyls wherein intermolecular covalent bonding can occur in multiple dimensions. Further disclosed are compositions comprising the disclosed compounds and process for the preparation thereof. The disclosed compounds are useful in electronic applications wherein from 2 to 100 layers of the disclosed compounds can be used to convey a current across the layer. The disclosed compounds are useful in the manufacture of transparent electrodes that are used in light-emitting diodes, touchscreens, antistatic coatings, flexible circuits, thin film solar cells, thin film thermoelectrics, or electrochromic coatings. Unlike prior art compounds which are anodic thereby moving "holes" the disclosed compounds are cathodic and therefore move electrons.

Disclosed herein are compounds having the formula:

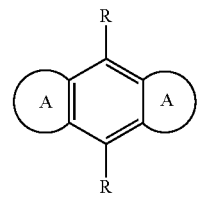

wherein A is a substituted or unsubstituted aryl unit containing 2 or more rings; and; R is chosen from substituted or unsubstituted aryl.

In one category the R units of the disclosed compounds can have one or more substitutions for hydrogen that are independently chosen from:

i) $OR^1$, $R^1$ chosen from hydrogen, substituted or unsubstituted $C_1$-$C_{18}$ linear, branched or cyclic alkyl, substituted or unsubstituted phenyl, said substitutions chosen from hydroxyl, $C_1$-$C_{18}$ linear, branched or cyclic alkyl, or mixtures thereof;

ii) $NR^2R^2$, each $R^2$ is independently chosen from hydrogen, $C_1$-$C_4$ linear, branched or cyclic alkyl, or mixtures thereof;

iii) substituted or unsubstituted $C_1$-$C_{18}$ linear, branched or cyclic alkyl, said substitutions chosen from hydroxyl, $C_1$-$C_8$ linear, branched or cyclic alkyl, phenyl, or mixtures thereof;

iv) substituted or unsubstituted aryl chosen from phenyl, naphthyl, phenanthrenyl, fluorenyl, of mixtures thereof, and v) substituted or unsubstituted heteroaryl;

wherein A can contain one or more free radicals.

Non-limiting examples of A units in this category include compounds wherein each A unit is independently chosen from:

i)

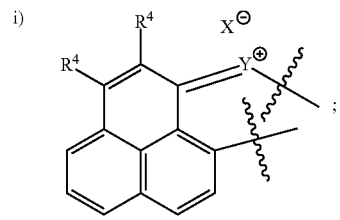

ii)

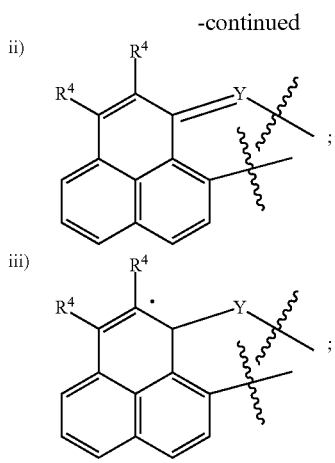

iii)

or
iv) mixtures thereof;
each $R^4$ is independently chosen from:
i) hydrogen;
ii) $OR^5$, $R^5$ chosen from hydrogen, substituted or unsubstituted $C_1$-$C_{18}$ linear, branched or cyclic alkyl, substituted or unsubstituted phenyl, said substitutions chosen from hydroxyl, $C_1$-$C_4$ linear, branched or cyclic alkyl, or mixtures thereof,
iii) $NR^6R^6$, each $R^6$ is independently chosen from hydrogen, $C_1$-$C_4$ linear, branched or cyclic alkyl, or mixtures thereof;
iv) substituted or unsubstituted $C_1$-$C_{18}$ linear, branched or cyclic alkyl, said substitutions chosen from hydroxyl, $C_1$-$C_4$ linear, branched or cyclic alkyl, phenyl, or mixtures thereof; or
v) a polyethylene glycol unit having the formula:

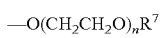

$R^7$ is hydrogen or $C_1$-$C_4$ alkyl, the index n is from about 5 to about 500;
each Y is independently chosen from O, $NR^3$, S, P, SO, $SO_2$, PO, NO, $C(R^8)_2$, or mixtures thereof;
each $R^3$ is chosen from hydrogen, substituted or unsubstituted $C_1$-$C_4$ linear, branched or cyclic alkyl, or mixtures thereof;
each $R^8$ is independently chosen from:
i) $OR^9$, $R^9$ chosen from hydrogen, substituted or unsubstituted $C_1$-$C_4$ linear, branched or cyclic alkyl, substituted or unsubstituted phenyl, said substitutions chosen from hydroxyl, $C_1$-$C_4$ linear, branched or cyclic alkyl, or mixtures thereof,
ii) $NR^{10}R^{10}$, each $R^{10}$ is independently chosen from hydrogen, $C_1$-$C_4$ linear, branched or cyclic alkyl, or mixtures thereof; or
iii) substituted or unsubstituted $C_1$-$C_6$ linear, branched or cyclic alkyl, said substitutions chosen from hydroxyl, $C_1$-$C_4$ linear, branched or cyclic alkyl, phenyl, or mixtures thereof;
each X is an anion independently chosen from halogen, $BF_4^-$, $ClO_4^-$, triflate, mesylate, tosylate, or mixtures thereof.

In one iteration when one R unit is unsubstituted phenyl both R units are unsubstituted phenyl. In another iteration when one R unit is $C_1$-$C_{18}$ linear substituted phenyl both R units are $C_1$-$C_{18}$ linear substituted phenyl. Non-limiting examples of alkyl substituted R units includes 4-methylphenyl, 4-ethylphenyl, 4-propylphenyl, 4-isopropylphenyl, 3,5-dimethylphenyl, 3,5-diethylphenyl, 3-methylphenyl, or 3-ethylphenyl.

Non-limiting examples of $R^4$ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy. $R^4$ units can be a mixture of different $R^4$ units.

The disclosed compounds can have two A rings having different substitution patterns, i.e., $R^4$ units. The following are non-limiting examples of A rings wherein the $R^4$ units which are not the same:

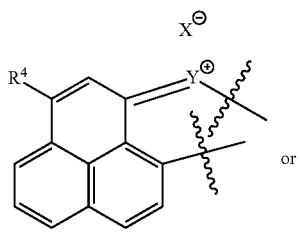

or

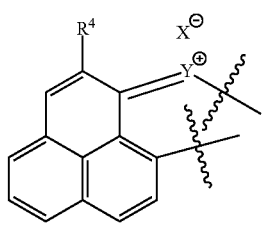

wherein the $R^4$ unit present can be any of the $R^4$ units recited herein above.

The following are non-limiting examples of this iteration:

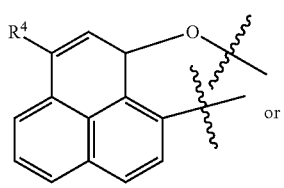

or

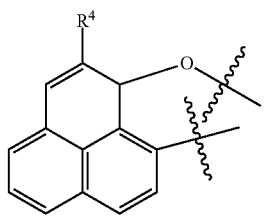

wherein $R^4$ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy.

The following are further non-limiting examples of this iteration:

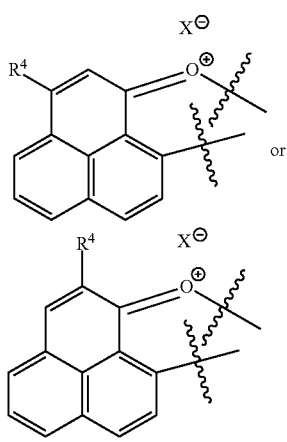

or

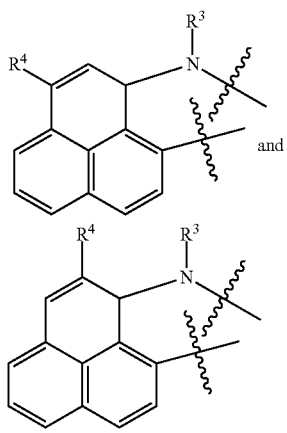

wherein $R^4$ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy.

In a further embodiment, a disclosed compound can have the following A units:

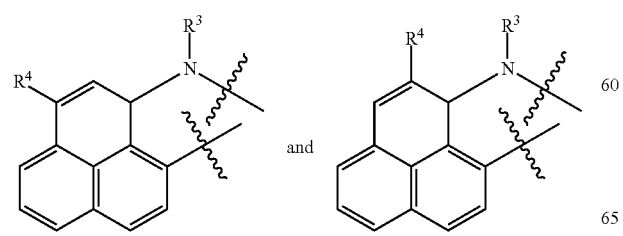

and wherein each $R^3$ is chosen from hydrogen, substituted or unsubstituted $C_1$-$C_4$ linear, branched or cyclic alkyl, or mixtures thereof, $R^4$ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy.

In a still further embodiment, a disclosed compound can have the following A units:

wherein each $R^3$ is chosen from hydrogen, substituted or unsubstituted $C_1$-$C_4$ linear, branched or cyclic alkyl, or mixtures thereof, $R^4$ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy.

In a yet still further embodiment, the disclosed compounds can have the following A units:

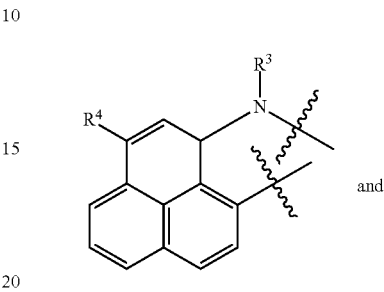

and

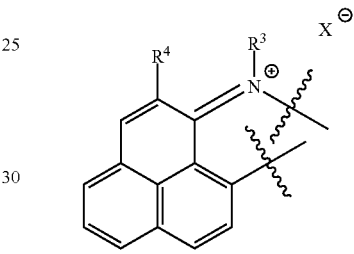

wherein each $R^3$ is chosen from hydrogen, substituted or unsubstituted $C_1$-$C_4$ linear, branched or cyclic alkyl, or mixtures thereof, $R^4$ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy. In one iteration $R^3$ is methyl.

In a yet another embodiment, the disclosed compounds can have the following A units:

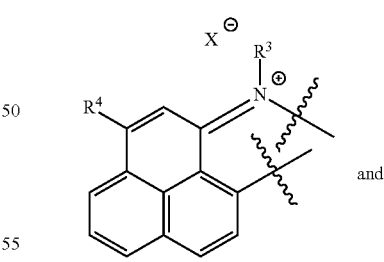

and

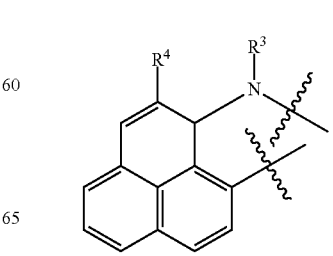

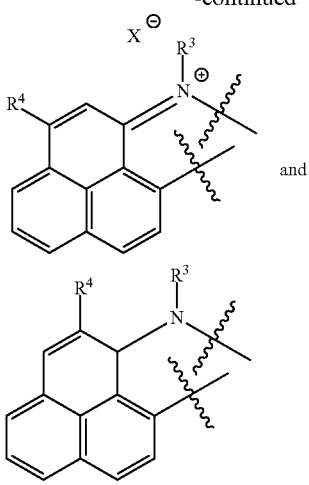

wherein each R³ is chosen from hydrogen, substituted or unsubstituted $C_1$-$C_4$ linear, branched or cyclic alkyl, or mixtures thereof, R⁴ units include hydrogen, hydroxyl, $C_1$-$C_3$ linear or branched alkyl, $C_1$-$C_3$ linear or branched alkoxy, for example, hydrogen, methyl, ethyl, propyl, isopropyl, methoxy, ethoxy, propoxy, or isopropoxy. In one iteration R³ is methyl.

As disclosed here in A units can be a mixture of rings having different charges, for example:

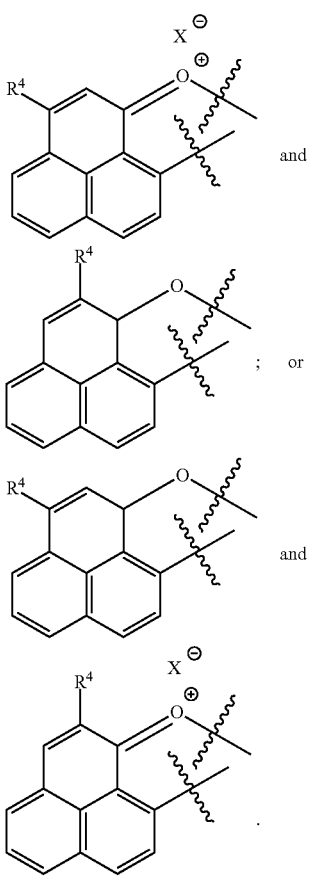

One aspect of the disclosed compounds relates to compounds having the formula:

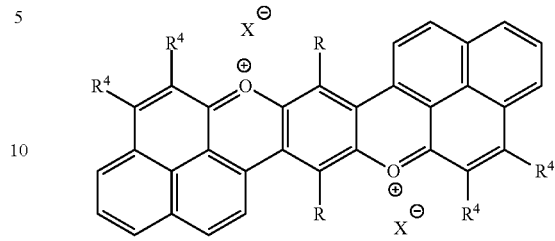

wherein R is chosen from substituted or unsubstituted phenyl, said substitutions are independently chosen from:
i) OR¹, R¹ chosen from hydrogen, substituted or unsubstituted $C_1$-$C_{18}$ linear, branched or cyclic alkyl, substituted or unsubstituted phenyl, said substitutions chosen from hydroxyl, $C_1$-$C_{18}$ linear, branched or cyclic alkyl, or mixtures thereof;
ii) NR²R², each R² is independently chosen from hydrogen, $C_1$-$C_4$ linear, branched or cyclic alkyl, or mixtures thereof;
iii) substituted or unsubstituted $C_1$-$C_{18}$ linear, branched or cyclic alkyl, said substitutions chosen from hydroxyl, $C_1$-$C_8$ linear, branched or cyclic alkyl, phenyl, or mixtures thereof;
iv) substituted or unsubstituted aryl chosen from phenyl, naphthyl, phenanthrenyl, fluorenyl, of mixtures thereof, and
v) substituted or unsubstituted heteroaryl;

each R⁴ is independently chosen from:
i) OR⁵, R⁵ chosen from hydrogen, substituted or unsubstituted $C_1$-$C_{18}$ linear, branched or cyclic alkyl, substituted or unsubstituted phenyl, said substitutions chosen from hydroxyl, $C_1$-$C_4$ linear, branched or cyclic alkyl, or mixtures thereof;
ii) NR⁶R⁶, each R⁶ is independently chosen from hydrogen, $C_1$-$C_4$ linear, branched or cyclic alkyl, or mixtures thereof;
iii) substituted or unsubstituted $C_1$-$C_{18}$ linear, branched or cyclic alkyl, said substitutions chosen from hydroxyl, $C_1$-$C_4$ linear, branched or cyclic alkyl, phenyl, or mixtures thereof; or
iv) a polyethylene glycol unit having the formula:

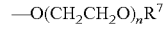
—O(CH₂CH₂O)$_n$R⁷

R⁷ is hydrogen or $C_1$-$C_4$ alkyl, the index n is from about 5 to about 500;
each X is an anion independently chosen from halogen, $BF_4^-$, $ClO_4^-$, triflate, mesylate, tosylate, or mixtures thereof.

One embodiment of this aspect relates to compounds having the formula:

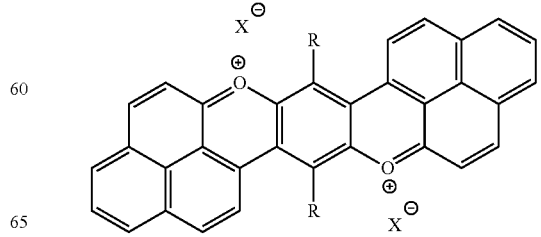

wherein R is chosen from substituted or unsubstituted phenyl, said substitutions are independently chosen from substituted or unsubstituted phenyl, naphthyl, phenanthrenyl, fluorenyl, of mixtures thereof. Each X is an anion independently chosen from halogen, $BF_4^-$, $ClO_4^-$, triflate, mesylate, tosylate, or mixtures thereof.

In one iteration of this embodiment of this aspect, the disclosed compounds have the formula:

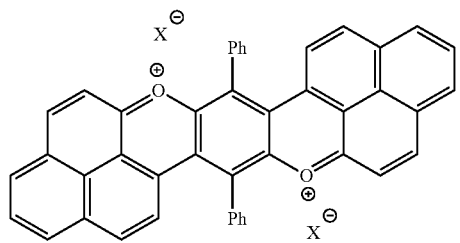

X is an anion independently chosen from halogen, $BF_4^-$, $ClO_4^-$, triflate, mesylate, or tosylate.

The following non-limiting example of the disclosed compounds according to this aspect can be prepared according to Scheme I and as described in Example 1.

Scheme 1

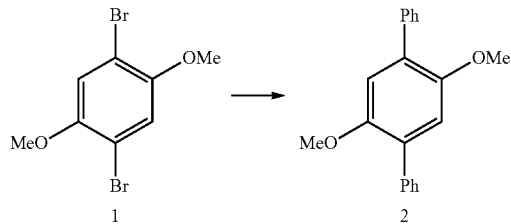

Reagents and Conditions: a) PdPPh4, PhB(OH)2, K2CO3

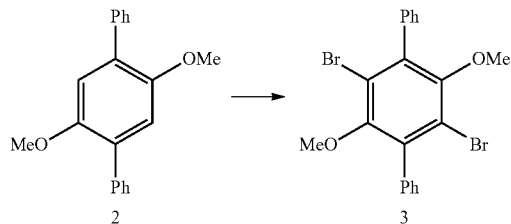

Reagents and Conditions: b) NBS, NH4NO3

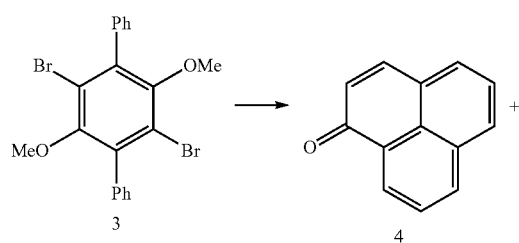

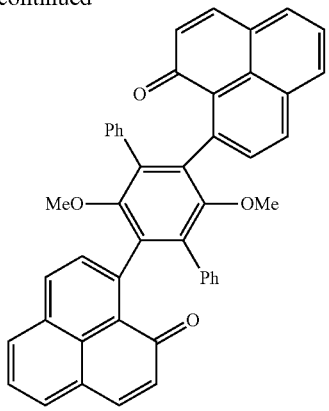

Reagents and Conditions: c) sBuLi, TMEDA, then 5, then DDQ

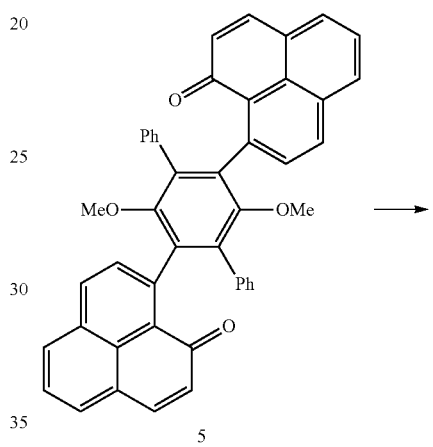

Reagents and Conditions: d) TfOH, TCE

Example 1

3a1,5a1-Dihydronaphtho[2,1,8-mna]naphtho[2',1',8': 4,5,6]-chromeno[3,2-i]xanthene-6,15-diium [(Ph2-PCPL)$^{2+}$ bis(trifluoromethanesulfonate)] (6)

Preparation of 2',5'-dimethoxy-1,1':4',1''-terphenyl (2) A flame dried RBF was charged with 1,4-dibromo-2,5-dimethoxybenzene (1) (10.3 g, 39.6 mmol, 1.0 equiv.), phenylboronic acid (9.92 g, 81.4 mmol, 2.05 equiv.), potassium carbonate (19.2 g, 139 mmol, 3.5 equiv.), toluene (80 mL), deionized water (40 mL), and a stir bar. Pd(PPh3)4 (457 mg, 0.395 mmol, 1 mol %) was added last to the flask before the reaction mixture was lowered into a bath that was preheated to 90° C. and stirred for 12 h with a condenser. Upon completion, the reaction was diluted with water, extracted 3 times with DCM, dried on MgSO4, and concentrated via rotary evaporation. The solid was then recrystallized in EtOH to provide 9.01 g (31.1 mmol, 78% yield) of white needles. $^1$H NMR (500 MHz, CDCl$_3$): δ 7.61-7.59 (m, 4H), 7.46-7.43 (m, 4H), 7.38-7.34 (m, 2H), 6.99 (s, 2H), 3.80 (s, 6H). $^{13}$C NMR (125 MHz, CDCl$_3$): δ 150.6, 138.3, 130.4, 129.4, 128.1, 127.1, 114.8, 56.4. HRMS (TOF-EI, m z) calcd. for C$_{20}$H$_{18}$O$_2$ [M]$^+$: 290.1307; found: 290.1300.

Preparation of 2',5'-dibromo-3',6'-dimethoxy-1,1':4',1''-terphenyl (3): A flame dried RBF was charged with, 2, (4.0 g, 13.8 mmol, 1.0 equiv.), ammonium nitrate (221 mg, 2.76 mmol, 0.2 equiv.), acetonitrile (250 mL) and a stir bar. N-Bromosuccinimide (6.14 g, 34.5 mmol, 2.5 equiv.) was added portionwise to the reaction flask and the reaction was allowed to stir for 24 h at room temperature. Upon completion, the reaction was washed with H$_2$O, extracted 3 times with DCM, dried on MgSO$_4$, and concentrated via rotary evaporation. The solid was then recrystallized in AcOH to provide 5.26 g (11.8 mmol, 86% yield) of white crystals. $^1$H NMR (500 MHz, CDCl$_3$): δ 7.50-7.41 (m, 6H), 7.38-7.36 (m, 4H), 3.42 (s, 6H). $^{13}$C NMR (125 MHz, CDCl$_3$): δ 151.9, 137.9, 136.8, 129.9, 128.1, 128.0, 119.3, 60.6. HRMS (TOF-EI, m z) calcd. for C$_{20}$H$_{16}$O$_2$Br$_2$ [M]+: 445.9517; found: 445.9555.

9,9'-([1,1':4',1''-terphenyl]-2',5'-diyl)bis(2,3-dihydro-1H-phenalen-1-one). (11): A flame dried RBF was charged with CuCl (14.0 mg, 0.141 mmol, 5 mol %), NaOtBu (19.0 mg, 0.197 mmol, 7 mol %), and rac-BINAP (87.8 mg, 0.141 mmol, 5 mol %). The flask was evacuated and backfilled 3 times with N2. Toluene (2 mL) was added and the flask was stirred for 20 min at room temperature. Polymethylhydrosiloxane (PMHS, 804.4 μL, 0.423 mmol, 15 mol %, 9 equiv. of SiH) was added and the resulting solution turned bright orange. A solution of 10 (1.655 g, 2.82 mmol, 1.0 equiv.) in DCM (65 mL) and $^i$PrOH (1.08 mL, 14.1 mmol, 5.0 equiv.) was added via syringe to the reaction, which was then stirred at room temperature for 12 hours. Upon completion it was quenched by slow addition of concentrated KOH in methanol. The mixture was extracted 3 times with diethyl ether, dried on MgSO$_4$, and concentrated under rotary evaporation. Purification via column chromatography (2% MeOH/DCM) furnished 1.630 g (2.76 mmol, 98% yield) of a light yellow solid. $^1$H NMR (400 MHz, CDCl$_3$): δ 7.99 (d, J=8.5 Hz, 2H), 7.77 (d, J=8.0 Hz, 2H), 7.62 (d, J=8.5 Hz, 2H), 7.45 (dd, J=7.5, 8.0 Hz, 2H), 7.39 (s, 2H), 7.36 (d, J=7.0 Hz, 2H), 7.17-7.14 (m, 4H), 7.09-7.05 (m, 6H), 3.33-3.25 (m, 4H), 2.64-2.58 (m, 2H), 2.16-2.12 (m, 2H). $^{13}$C NMR (125 MHz, CDCl$_3$): δ 200.1, 141.0, 139.6, 139.5, 139.4, 133.7, 132.5, 132.1, 131.9, 131.3, 130.8, 130.2, 130.1, 129.4, 127.7, 126.2, 126.1, 125.9, 125.6, 39.6, 29.9. HRMS (ESI, m z) calcd. for C$_{44}$H$_{31}$O$_2$ [M+H]$^+$: 591.2319; found: 591.2326.

Preparation of (Ph$_2$-PCPL)$^{2+}$ bis(trifluoromethanesulfonate) (6) A screw top vial was charged with 1,1,2,2-tetrachloroethane (TCE, 1 mL) and trifluoromethanesulfonic acid (68.3 μL, 0.773 mmol, 5 equiv.). A solution of 5 (100 mg, 0.155 mmol, 1 equiv.) in TCE (5 mL) was added to the vial dropwise, and then the entire reaction mixture was allowed to stir at 120° C. for 12 h, during which time the reaction changed from a dark red to magenta color. Afterwards, the mixture added to diethyl ether to precipitate a metallic brown solid, which was collected by filtration. (90.0 mg, 0.1391 mmol, 90% yield). $^1$H NMR (400 MHz, 1:1 CD$_3$CN:CF$_3$COOD) δ 9.28 (d, J=8.8 Hz, 2H), 9.13 (d, J=7.6 Hz, 2H), 9.05 (d, J=8.0 Hz, 2H), 9.00 (d, J=9.2 Hz, 2H), 8.51 (t, J=7.6 Hz, 2H), 8.25 (d, J=8.8 Hz, 2H), 8.10 (d, J=8.8 Hz, 2H), 7.88-7.83 (6H), 7.73-7.71 (4H). $^{13}$C NMR (100 MHz, CD$_3$CN): δ165.6, 151.5, 148.6, 147.3, 144.7, 144.3, 142.6, 134.9, 133.5, 132.5, 131.5, 131.4, 131.3, 131.2, 129.0, 127.9, 123.6, 121.9, 120.7, 117.9. $^{19}$F NMR (100 MHz, CF$_3$COOH) –79.28. HRMS (ESI, m z) calcd. for C$_{44}$H$_{24}$O$_2$ [M]$^{2+}$: 292.0883; found: 292.0883.

Another aspect of the disclosed compounds relates to compounds having the formula:

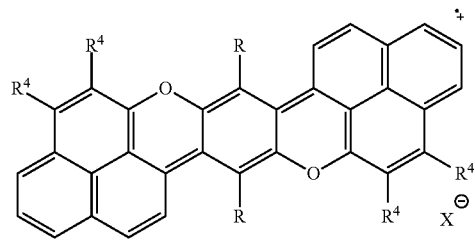

wherein R is chosen from substituted or unsubstituted phenyl, said substitutions are independently chosen from:

i) OR$^1$, R$^1$ chosen from hydrogen, substituted or unsubstituted C$_1$-C$_{18}$ linear, branched or cyclic alkyl, substituted or unsubstituted phenyl, said substitutions chosen from hydroxyl, C$_1$-C$_{18}$ linear, branched or cyclic alkyl, or mixtures thereof;

ii) NR$^2$R$^2$, each R$^2$ is independently chosen from hydrogen, C$_1$-C$_4$ linear, branched or cyclic alkyl, or mixtures thereof;

iii) substituted or unsubstituted C$_1$-C$_{18}$ linear, branched or cyclic alkyl, said substitutions chosen from hydroxyl, C$_1$-C$_8$ linear, branched or cyclic alkyl, phenyl, or mixtures thereof;

iv) substituted or unsubstituted aryl chosen from phenyl, naphthyl, phenanthrenyl, fluorenyl, of mixtures thereof, and v) substituted or unsubstituted heteroaryl;

each R$^4$ is independently chosen from:

i) OR$^5$, R$^5$ chosen from hydrogen, substituted or unsubstituted C$_1$-C$_{18}$ linear, branched or cyclic alkyl, substituted or unsubstituted phenyl, said substitutions chosen from hydroxyl, C$_1$-C$_4$ linear, branched or cyclic alkyl, or mixtures thereof, ii) NR$^6$R$^6$, each R$^6$ is independently chosen from hydrogen, C$_1$-C$_4$ linear, branched or cyclic alkyl, or mixtures thereof;

iii) substituted or unsubstituted C$_1$-C$_{18}$ linear, branched or cyclic alkyl, said substitutions chosen from hydroxyl, C$_1$-C$_4$ linear, branched or cyclic alkyl, phenyl, or mixtures thereof; or iv) a polyethylene glycol unit having the formula:

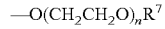

R$^7$ is hydrogen or C$_1$-C$_4$ alkyl, the index n is from about 5 to about 500; each X is an anion independently chosen from halogen, BF$_4^-$, ClO$_4^-$, triflate, mesylate, tosylate, or mixtures thereof.

One embodiment of this aspect relates to compounds having the formula:

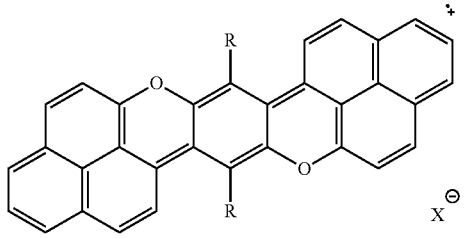

wherein R is chosen from substituted or unsubstituted phenyl, said substitutions are independently chosen from substituted or unsubstituted phenyl, naphthyl, phenanthrenyl, fluorenyl, of mixtures thereof. X is an anion independently chosen from halogen, $BF_4^-$, $ClO_4^-$, triflate, mesylate, or tosylate.

In one iteration of this embodiment of this aspect, the disclosed compounds have the formula:

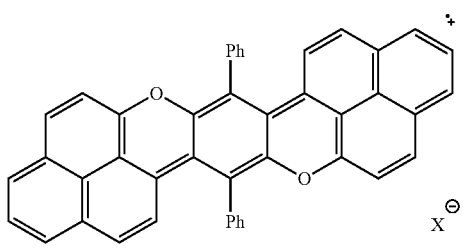

wherein X is an anion independently chosen from halogen, $BF_4^-$, $ClO_4^-$, triflate, mesylate, tosylate.

The following non-limiting example of the disclosed compounds according to this aspect can be prepared according to Scheme II and as described in Example 2.

Scheme 2

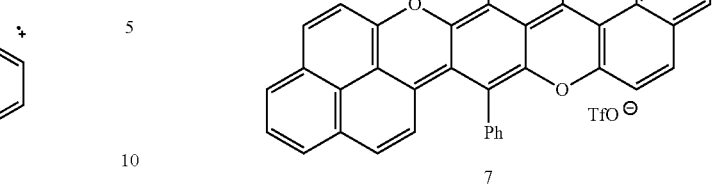

Reagents and Conditions: a) $Na_2S_2O_4$

Example 2

[(Ph₂-PCPL)]⁺ trifluoromethanesulfonate (7)

Preparation of (Ph₂-PCPL)⁺ trifluoromethanesulfonate (7): A screw top vial was charged with acetonitrile (CH₃CN, 3 mL) and, 6, (120 mg, 0.136 mmol, 1 equiv.), the mixture was allowed to stir for 20 min at ambient conditions, during which time 4 went into solution furnishing a purple solution. Afterwards, Na₂S₂O₄ (473.6 mg, 2.72 mmol, 20 equiv.) was added to the solution and it was allowed to stir at room temperature for 2 h, during which the solution changed to an indigo color. The mixture was then washed with H₂O and CH₃CN and concentrated via rotary evaporation to provide a dark blue solid (93.2 mg, 0.127 mmol, 93% yield). HRMS (ESI, m z) calcd. for $C_{44}H_{25}O_2$ [M+H]⁺: 585.1849; found: 585.1833. Crystals suitable for X-ray diffraction were grown by diethyl ether (Et₂O) diffusion into a 1,1,2,2-tetrachloroethane (TCE)/acetonitrile solution of 7.

A further aspect of the disclosed compounds relates to compounds having the formula:

wherein R is chosen from substituted or unsubstituted phenyl, said substitutions are independently chosen from:
i) OR¹, R¹ chosen from hydrogen, substituted or unsubstituted $C_1$-$C_{18}$ linear, branched or cyclic alkyl, substituted or unsubstituted phenyl, said substitutions chosen from hydroxyl, $C_1$-$C_{18}$ linear, branched or cyclic alkyl, or mixtures thereof;
ii) NR²R², each R² is independently chosen from hydrogen, $C_1$-$C_4$ linear, branched or cyclic alkyl, or mixtures thereof;

iii) substituted or unsubstituted $C_1$-$C_{18}$ linear, branched or cyclic alkyl, said substitutions chosen from hydroxyl, $C_1$-$C_8$ linear, branched or cyclic alkyl, phenyl, or mixtures thereof;

iv) substituted or unsubstituted aryl chosen from phenyl, naphthyl, phenanthrenyl, fluorenyl, of mixtures thereof, and v) substituted or unsubstituted heteroaryl;

each $R^2$ is independently chosen from hydrogen, $C_1$-$C_4$ linear, branched or cyclic alkyl, or mixtures thereof;

each $R^4$ is independently chosen from:

i) $OR^5$, $R^5$ chosen from hydrogen, substituted or unsubstituted $C_1$-$C_{18}$ linear, branched or cyclic alkyl, substituted or unsubstituted phenyl, said substitutions chosen from hydroxyl, $C_1$-$C_4$ linear, branched or cyclic alkyl, or mixtures thereof, ii) $NR^6R^6$, each $R^6$ is independently chosen from hydrogen, $C_1$-$C_4$ linear, branched or cyclic alkyl, or mixtures thereof;

iii) substituted or unsubstituted $C_1$-$C_{18}$ linear, branched or cyclic alkyl, said substitutions chosen from hydroxyl, $C_1$-$C_4$ linear, branched or cyclic alkyl, phenyl, or mixtures thereof; or iv) a polyethylene glycol unit having the formula:

—O(CH$_2$CH$_2$O)$_n$R$^7$ $R^7$ is hydrogen or $C_1$-$C_4$ alkyl, the index n is from about 5 to about 500.

One embodiment of this aspect relates to compounds having the formula:

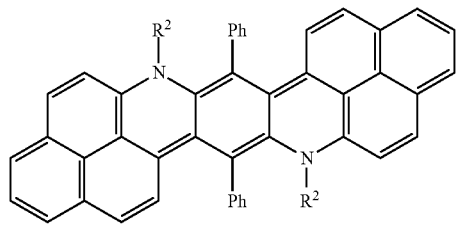

each $R^2$ is independently chosen from hydrogen, $C_1$-$C_4$ linear, branched or cyclic alkyl, or mixtures thereof.

Another embodiment of this aspect relates to compounds having the formula:

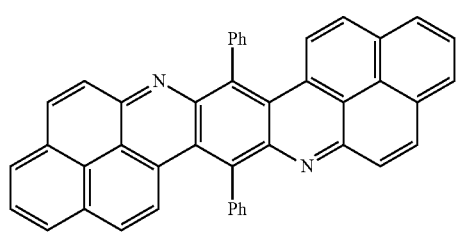 [SMILES: c1ccc(-c2c3nc4ccc5cccc6ccc(c3c(-c3ccccc3)c3nc7ccc8cccc9ccc(c23)c7c89)c4c56)cc1]

The following non-limiting example of the disclosed compounds according to this aspect can be prepared according to Scheme III and as described in Example 3.

Scheme III

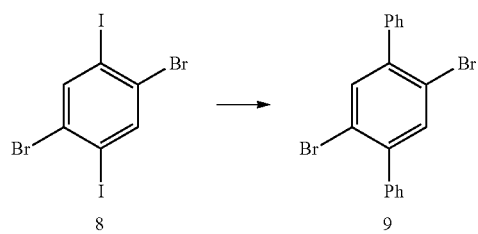

Reagents and Conditions: a) Pd$_2$dba$_3$/P(otol)$_3$, PhB(OH)$_2$, K$_2$CO$_3$,

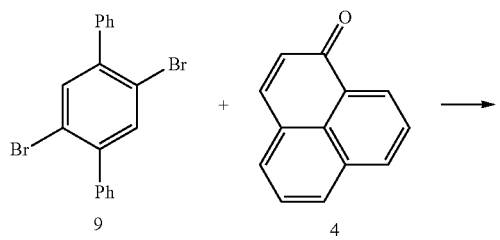

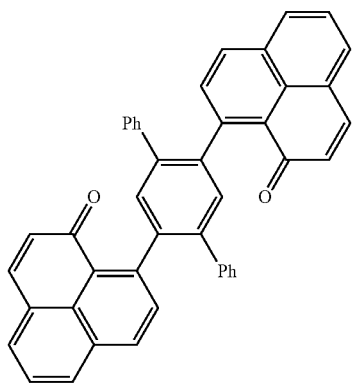

Reagents and Conditions: b) sBuLi, TMEDA, then 4, then DDQ

-continued

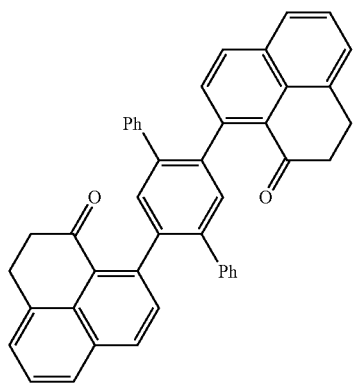

11

Reagents and Conditions: c) CuCl, NaOtBu, BINAP, PMHS

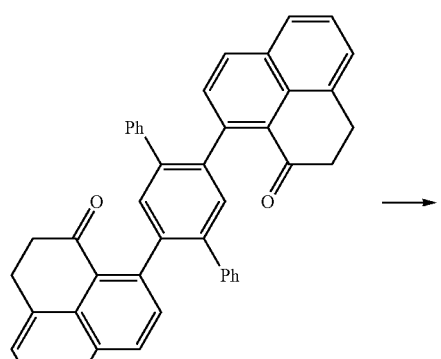

11

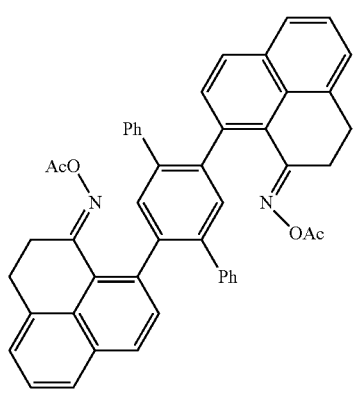

12

Reagents and Conditions: d) H₂NOH HCl, Ac₂O, pyridine

-continued

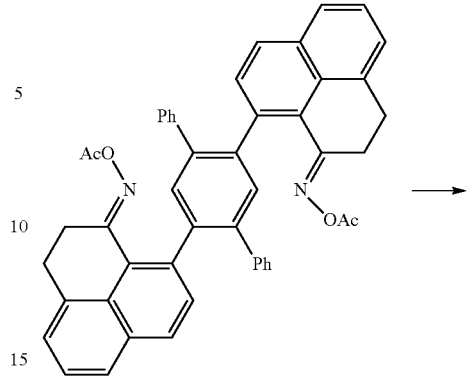

12

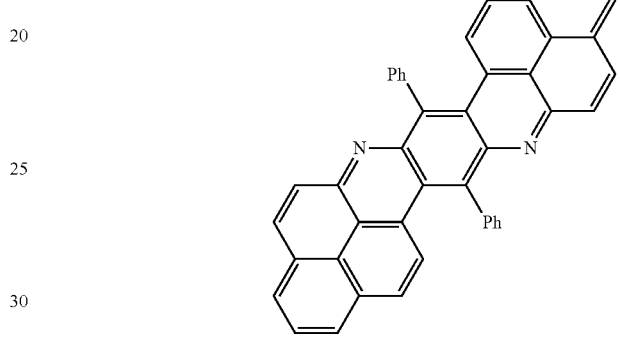

13

Reagents and Conditions: e) Fe(acac)₃

Example 3

7,16-Diphenyl-5a,6,14a,15-tetrahydronaphtho[2,1,8-mna]naphtho[2',1',8':4,5,6]-quinolino[3,2-i]acridine (13)

Preparation of 2',5'-dibromo-1,1':4',1''-terphenyl (9): can be prepared via cross-couling of phenylboronic acid and 1,4-dibromo-2,5-diiodobenzene. 9,9'-([1,1':4',1''-terphenyl]-2',5'-diyl)bis(1H-phenalen-1-one) (10). A flame dried RBF was charged with 9 (1.940 g, 5.02 mmol, 1.0 equiv.). The flask was backfilled with nitrogen and TMEDA (3.09 mL, 20.6 mmol, 4.1 equiv.) was added along with 30 mL dry THF. The solution was cooled to −78° C. for 20 min before 1.3M sBuLi in hexanes (15.76 mL, 20.5 mmol, 4.1 equiv.) was added dropwise. The reaction was left to stir at −78° C. for 45 min. Then phenalenone (4) (1.89 g, 10.5 mmol, 2.1 equiv) dissolved in dry THE (20 mL) was added slowly to the reaction mixture. The reaction was kept at −78° C. for 20 min before warming to room temperature and allowed to stir overnight. The reaction was quenched with saturated $NH_4C_1$ and extracted with DCM to yield a suspension. The reaction was then concentrated to a slurry via rotary evaporation and filtered through a 0.22 m nylon filter. The resulting orange solid was then transferred into a 100 mL round bottom flask, which was subsequently charged with DCM (50 mL) and DDQ (2.27 g, 10.0 mmol, 2.0 equiv.). The flask was heated to 50° C. and allowed to stir for 1 hour. The reaction was poured into a separation funnel followed by 20 mL of a 4M NaOH solution. The separation funnel was shaken vigorously until the organic layer turned orange, which was then extracted 3 times with DCM, dried under MgSO$_4$, and concentrated under rotary evaporation to furnish 1.985 g (3.38 mmol, 68% yield) of an orange solid, 10. $^1$H NMR (500 MHz, CDCl$_3$): δ 8.02 (d, J=8.5 Hz, 2H), 7.97 (d, J=8.0 Hz, 2H), 7.74 (d, J=6.5 Hz, 2H), 7.67 (d, J=10.0 Hz, 2H), 7.60 (d, J=8.5 Hz, 2H), 7.57 (dd, J=8.0, 8.0 Hz, 2H), 7.42 (s, 2H), 7.26-7.22 (m, 4H), 7.05-7.01 (m, 6H), 6.59 (d, J=9.5 Hz, 2H). $^{13}$C NMR (100 MHz, CDCl$_3$): δ 185.7, 147.5, 141.1, 140.6, 140.3, 138.6, 133.3, 132.8, 131.7, 131.3, 131.1, 130.8, 130.2, 129.7, 128.2, 128.1, 127.5, 127.1, 126.3, 126.1. HRMS (ESI, m z) calcd. for C$_{44}$H$_{27}$O$_2$ [M+H]$^+$: 587.2006; found: 587.2008.

Preparation of 9,9'-([1,1':4',1''-terphenyl]-2',5'-diyl)bis (1H-phenalen-1-one) (10): Compound 10 can be prepared using the same reaction conditions utilized above to prepare compound 5. 2',5'-dibromo-1,1':4',1''-terphenyl (9). A flame dried RBF was charged with 1,4-dibromo-2,5-diiodobenzene (18.4 g, 37.7 mmol, 1.0 equiv.), phenylboronic acid (9.7 g, 79.2 mmol, 2.1 equiv.), potassium carbonate (20.8 g, 150.8 mmol, 4.0 equiv.), toluene (100 mL), deionized water (25 mL), and a stir bar. (Pd$_2$dba$_3$) (172.6 mg, 0.189 mmol, 0.5 mol %) and P(o-tolyl)$_3$ (229.5 mg, 0.754 mmol, 2 mol %) were added last to the flask before the reaction mixture was lowered into a bath that was preheated to 90° C. and stirred for 12 h with a condenser. Upon completion, the reaction was diluted with water, extracted 3 times with DCM, dried on MgSO$_4$, and concentrated via rotary evaporation. The solid was then recrystallized in EtOH that provided 14.1 g (36.3 mmol, 96% yield) of white needles. $^1$H NMR (400 MHz, CDCl$_3$): δ 7.65 (s, 2H), 7.47-7.42 (m, 10H). $^{13}$C NMR (100 MHz, CDCl$_3$): δ 142.9, 139.4, 135.2, 129.3, 128.2, 128.1, 121.3. HRMS (TOF-EI, m z) calcd. for C$_{18}$H$_{12}$Br$_2$ [M]$^+$: 385.9306; found: 385.9306.

Preparation of 9,9-([1,1':4',1''-terphenyl]-2',5'-diyl)bis(2, 3-dihydro-1H-phenalen-1-one). (11): A flame dried RBF was charged with CuCl (14.0 mg, 0.141 mmol, 5 mol %, NaOtBu (19.0 mg, 0.197 mmol, 7 mol %), and rac-BINAP (87.8 mg, 0141 mmol, 5 mol %). The flask was evacuated and backfilled 3 times with N2. Toluene (2 mL) was added and the flask was stirred for 20 min. at room temperature. Polymethylhydrosiloxane (PMHS, 804.4 μL, 0.423 mmol, 15 mol %, 9 equiv. of SiH) was added and the resulting solution turned bright orange. A solution of 10 (1.655 g, 2.8 s mmol, 1.0 equiv.) in DCM (65 mL) and $^i$PrOH (1.08 mL, 14.1 mmol, 5.0 equiv.) was added via syringe to the reaction, which was then stirred at room temperature for 12 hours. Upon completion it was quenched by slow addition of concentrated KOH in methanol. The mixture was extracted 3 times with diethyl ether, dried on MgSO$_4$, and concentrated under rotary evaporation. Purification via column chromatography (2% MeOH/DCM) furnished 1.630 g (2.76 mmol, 98% yield) of a light yellow solid. $^1$H NMR (400 MHz, CDCl$_3$): δ 7.99 (d, J=8.5 Hz, 2H), 7.77 (d, J=8 Hz, 2H), 7.72 (J=8.5 Hz, 2H), 7.45 (dd, J=7.5, 8.0 Hz, 2H), 7.39 (s, 2H) 7.36 (d, J=7.0 Hz, 2H), 7.17-7.14 (m, 4H), 7.09-7.05 (m, 6H), 3.33-3.25 (m, 4H), 2.64-2.58 (m 2H), 2.16-2.12 (m, 2H). $^{13}$C NMR (125 MHz CDCl$_3$): d: 200.1, 141.0, 139.6, 139.5, 139.4, 133.7, 132.5, 132.1, 131.9, 131.3, 130.8, 130.2, 130.1, 129.4, 127.7, 126.2, 126.1, 125.9, 125.6, 39.6, 29.9. HRMS (ESI, m z) calcd. for C$_{44}$H$_{31}$O$_2$ [M+H]$^+$: 591.2319; found 591.2326.

Preparation of diphenyl-pyrido[2,3-g]quinoline-phenalenyl (Ph$_2$-PQPL) (13). A flame dried RBF was charged with diacetyl dioxime (12) (805.0 mg, 1.14 mmol, 1 equiv.), Fe(acac)$_3$ (604 mg, 1.71 mmol, 1.5 equiv.), and AcOH (40 mL) and allowed to stir at 90° C. for 12 hours. Upon completion the mixture was concentrated by rotary evaporation to remove AcOH. The dark residue was then washed with 3M NaOH (50 mL), extracted 3 times with DCM, dried on MgSO$_4$, and concentrated under rotary evaporation until the volume reached ca. 5 mL. The dark red DCM solution was then pipetted into an Erlenmeyer flask of hexanes (100 mL) to precipitate 549 mg (0.946 mmol, 83% yield) of a red solid. $^1$H NMR (400 MHz, CDCl$_3$): δ 8.20 (d, J=8.0 Hz, 2H), 8.16 (d, J=7.2 Hz, 2H), 8.12 (d, J=9.6 Hz, 2H), 8.04-7.95 (m, 8H), 7.74-7.70 (m, 4H), 7.69-7.65 (m, 6H).

A further embodiment of this aspect relates to compounds having the formula:

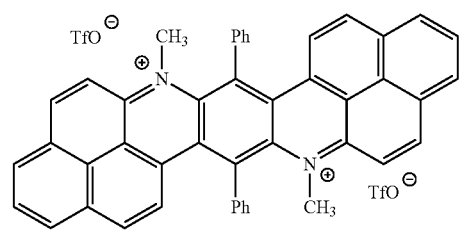 [SMILES: C[n+]1c2ccc3cccc4ccc(c5c(-c6ccccc6)c6c(c(-c7ccccc7)c51)c1ccc5cccc7ccc(c1c57)[n+]6C)c2c43]

The following non-limiting example of the disclosed compounds according to this aspect can be prepared according to Scheme IV and as described in Example 4.

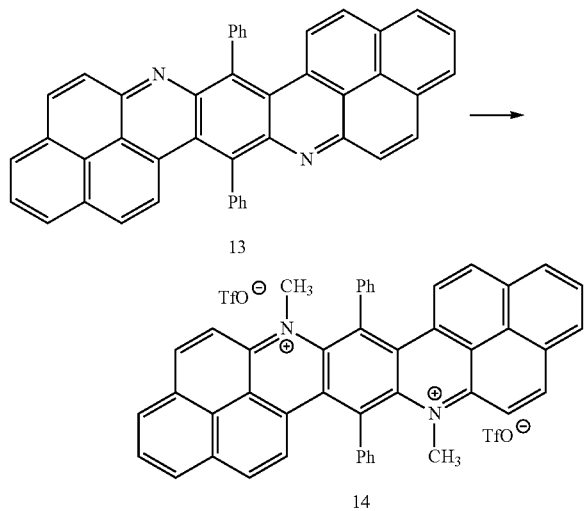

Reagents and Conditions: a) CH$_3$OTf

Example 4

Mono(6,15-dimethyl-7,16-diphenylnaphtho[2,1,8-mna]naphtho[2',1',8':4,5,6]-quinolino[3,2-i]acridine-6,15-diium) mono(trifluoromethanesulfonate) [(Ph$_2$-Me$_2$-PQPL)(OTf)$_2$]

Preparation of [(Ph$_2$-Me$_2$-PQPL)(OTf)$_2$, 14: A RBF that was oven dried overnight was charged with 13 (190.0 mg, 0.327 mmol, 1 equiv.) and 1,2-dichloroethane (25 mL). Methyl trifluoromethane-sulfonate (0.180 mL, 1.64 mmol, 5 equiv.) was added dropwise at 50° C. and the reaction was allowed to stir for 16 hours under N2. Upon completion the mixture was concentrated under rotary evaporation and then purified by column chromatography (4% EtOH/DCM) to furnish 169 mg (0.186 mmol, 57% yield) of a dark purple solid. $^1$H NMR (400 MHz, CH$_3$CN): δ 9.13 (d, J=9.6 Hz, 2H), 8.92 (d, J=7.2 Hz, 2H), 8.81 (d, J=7.6 Hz, 2H), 8.50 (d, J=8.8 Hz, 2H), 8.43 (t, J=7.6 Hz, 2H), 8.36 (d, J=9.2 Hz, 2H), 7.89-7.85 (m, 2H), 7.80-7.70 (m, 10H), 3.89 (s, 6H).

A yet further embodiment of this aspect relates to compounds having the formula:

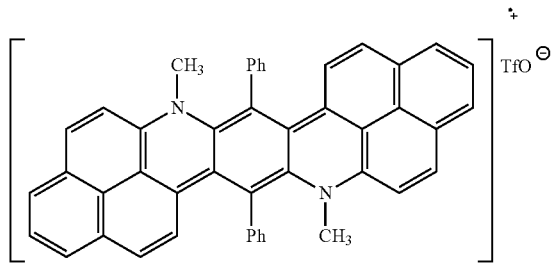

The following non-limiting example of the disclosed compounds according to this aspect can be prepared according to Scheme V and as described in Example 5.

Scheme V

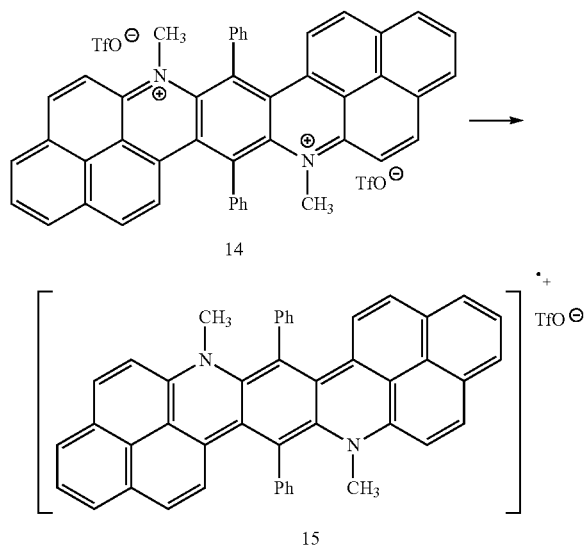

Reagents and Conditions: (a) Na$_2$S$_2$O$_4$

Example 5

6,15-Dimethyl-7,16-diphenyl-5a,6,14a,15-tetrahydronaphtho[2,1,8-mna]naphtho[2',1',8':4,5,6]quinolino[3,2-i]acridine [(Ph$_2$-Me$_2$-PQPL)(OTf)]

Preparation of (Ph$_2$-Me$_2$-PQPL)(OTf), 15: An oven dried RBF was charged with 14, (30 mg, 0.0330 mmol, 1 equiv.) acetonitrile (2 mL), DCM (4 mL) and 2 drops of AcOH. To this solution, sodium dithionite (28.7 mg, 0.165 mmol, 5 equiv.) was added, and allowed to stir at room temperature for 12 hours. Upon completion, the mixture was concentrated under rotary evaporation. The residue was then dissolved in DCM and filtered through a 20 m nylon filter to remove the inorganic salts and provide a purplish-blue solution. The solution was then precipitated in hexanes to furnish 24 mg (0.0313 mmol, 95% yield) of a dark blue solid. Single crystals grown in dichloroethane/hexanes were sufficient for single crystal X-ray analysis for confirmation of the molecular structure FIG. 1 is the UV-Vis-NIR spectrum of compound 7 measured at room temperature (298 K) with a Varian Cary 500 spectrophotometer. All solvents used for solution samples were dried and degassed before use. Thin-film measurements of compound 7 were collected by drop casting films from TCE. Wavelengths are shown in nanometers (nm), and absorption is reported in arbitrary units (arb. units). The top curve having a peak a λ=1859 nm was taken in a 1,1,2,2-tetrachloroethane solution and whereas the lower curve having a peak at λ=2008 nm was taken as a thin film.

Figure 2:
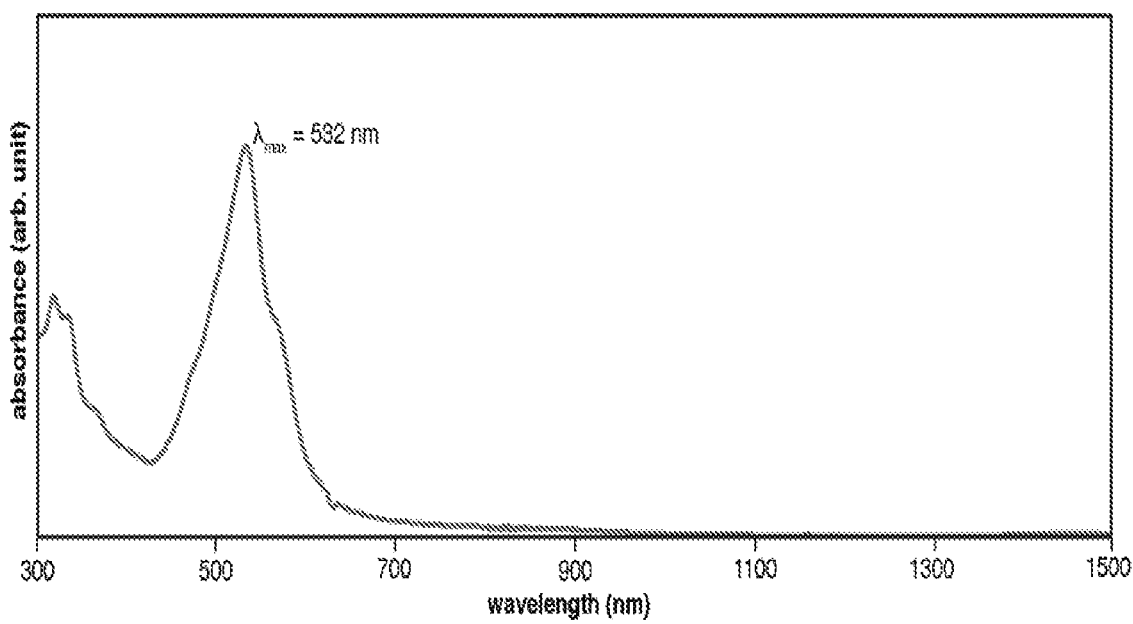
FIG. 2 is the absorption spectrum of compound 6 taken in acetonitrile.
Figure 3:
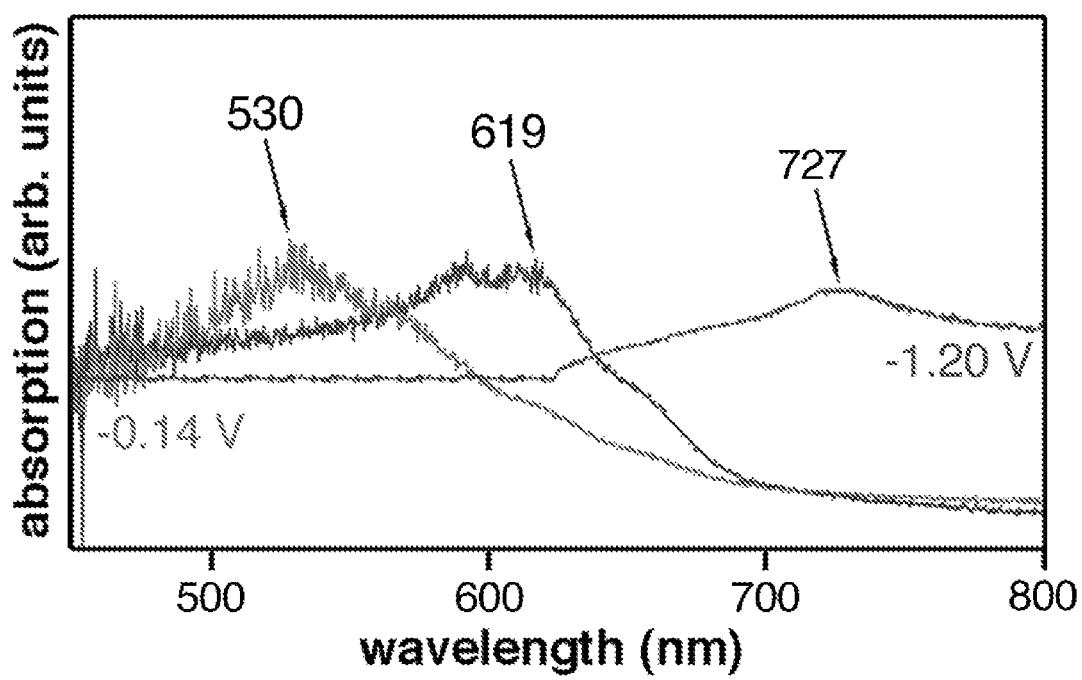
FIG. 3 depicts the spectroelectrochemical difference spectra of compound 7 at varying potentials to identify changes in absorption upon oxidation (−0.14 V) and reduction (−1.20 V, versus Fc/Fc$^+$ couple).
Figure 4:
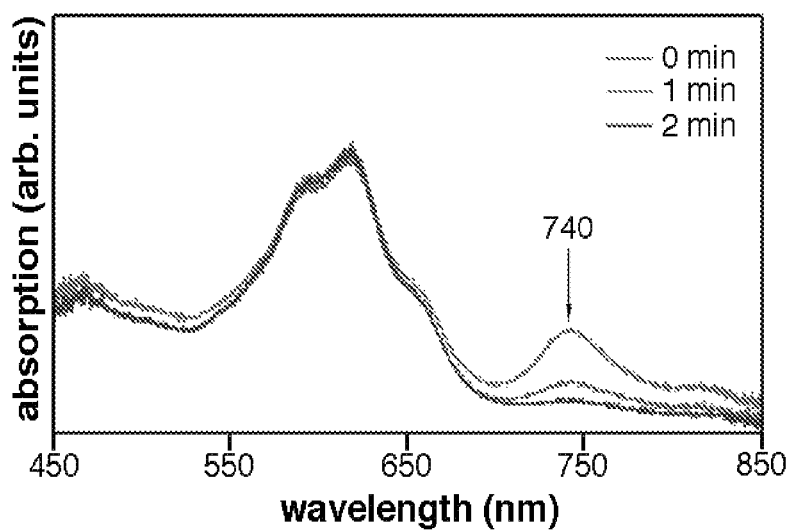
FIG. 4 is the absorption spectra of a crude reaction mixture of 6 reduced by $Na_2S_2O_4$ in 1,1,2,2-tetrachloroethane in the presence of 5 equiv. trifluoromethanesulfonic acid indicating the change of the peak at 750 nm over time.

FIG. 2 is the absorption spectrum of compound 6 taken in acetonitrile. The λ$_{max}$ of 532 nm is far up field of compound 7's λ$_{max}$ of 1859 nm. FIG. 4 is the absorption spectra of a crude reaction mixture of 6 reduced by Na$_2$S$_2$O$_4$ in 1,1,2, 2-tetrachloroethane in the presence of 5 equiv. trifluoromethanesufonic acid indicating the change of the peak at 750 nm over time. Upon stirring overnight, the mixture was diluted 10-fold and added to an open cuvette, where spectra were taken at 1 minute intervals. After 2 minutes, the 740 nm peak assigned to neutral 7 is nearly absent.

Figure 5:
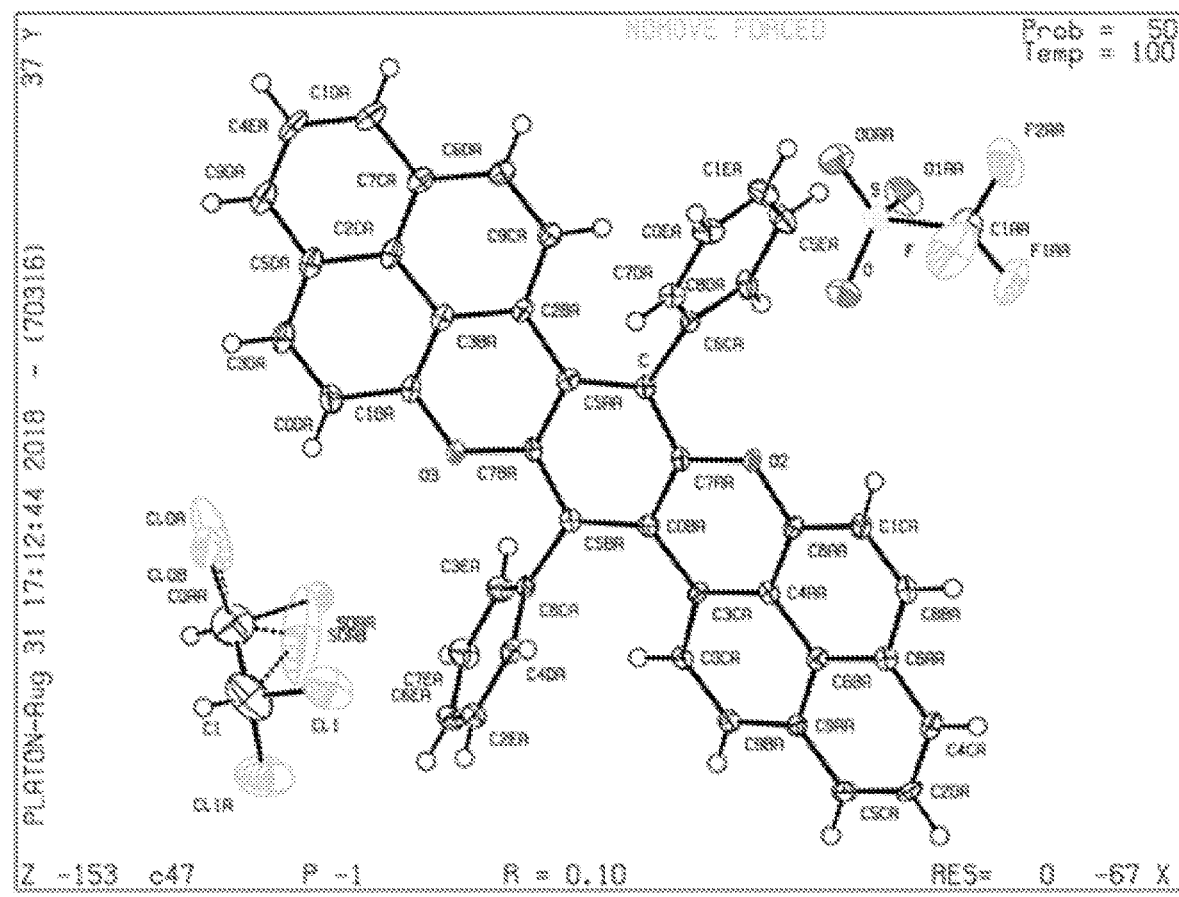
FIG. 5 is an ORTEP plot of compound 7.

FIG. 5 is an ORTEP diagram of compound 7. The following are the X-ray crystallographic data for this compound.

| | |
|---|---|
| Applicant's Identification code | (Ph$_2$-PCPL)(OTf) |
| Empirical formula | C$_{47}$Cl$_4$O$_5$H$_{25}$S$_1$F$_3$ |
| Formula weight | 901.23 |
| Temperature/K | 100 K |
| Crystal system | triclinic |
| Space group | P-1 |
| a/Å | 10.1047 (6) |
| b/Å | 14.1320 (7) |
| c/Å | 14.8352 (8) |
| α/° | 111.146(5) |
| β/° | 93.115(5) |
| γ/° | 104.921(5) |
| Volume/Å$^3$ | 1883.55(19) |
| Z | 2 |
| ρ$_{calc}$g/cm$^3$ | 1.589 |
| μ/mm$^{-1}$ | 0.44 |
| F (000) | 917 |
| Crystal size/mm$^3$ | 0.34 × 0.21 × 0.15 |
| Radiation | Mo Kα (λ = 0.71073) |
| 2Θ range for data collection/° | 2.4 to 23.2 |
| Index ranges | −14 ≤ h ≤ 14, −20 ≤ k ≤ 20, −21 ≤ 1 ≤ 21 |
| Reflections collected | 38938 |
| Independent reflections | 10414 [R$_{int}$ = 0.064] |
| Data/restraints/parameters | 10414/0/560 |
| Goodness-of-fit on F$^2$ | 1.029 |
| Final R indexes [I >= 2σ (I)] | R$_1$ = 0.0969, wR$_2$ = 0.3193 |
| Largest diff. peak/hole/e Å$^{-3}$ | 1.1/−1.6 |

Figure 6:
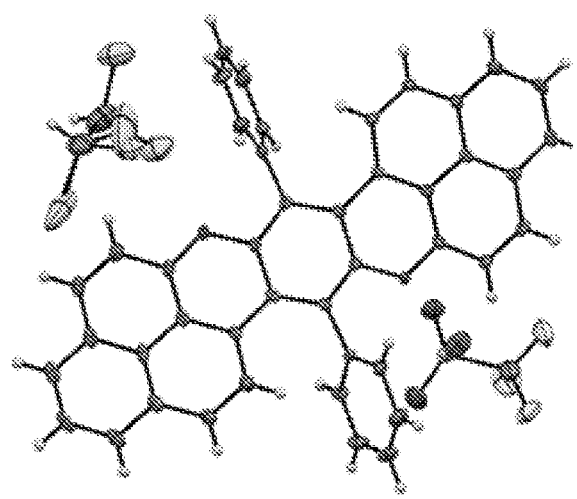
FIG. 6 is an ORTEP depiction of compound 7 showing the association of compound 7 with triflate anion and one TCE molecule.
Figure 7:
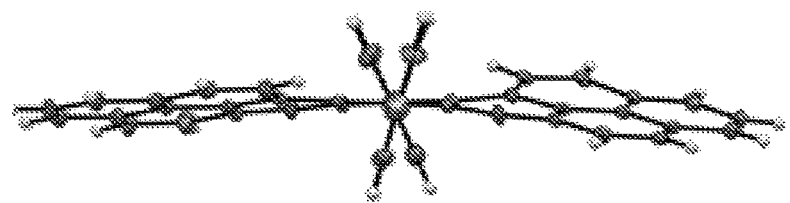
FIG. 7 is an ORTEP side view that shows the twisted topology of 7$^+$.

FIG. 6 is an ORTEP depiction of compound 7 showing the association of compound 7 with triflate anion and one TCE molecule. FIG. 7 is an ORTEP side view that shows the twisted topology of 7$^+$.

Figure 8:
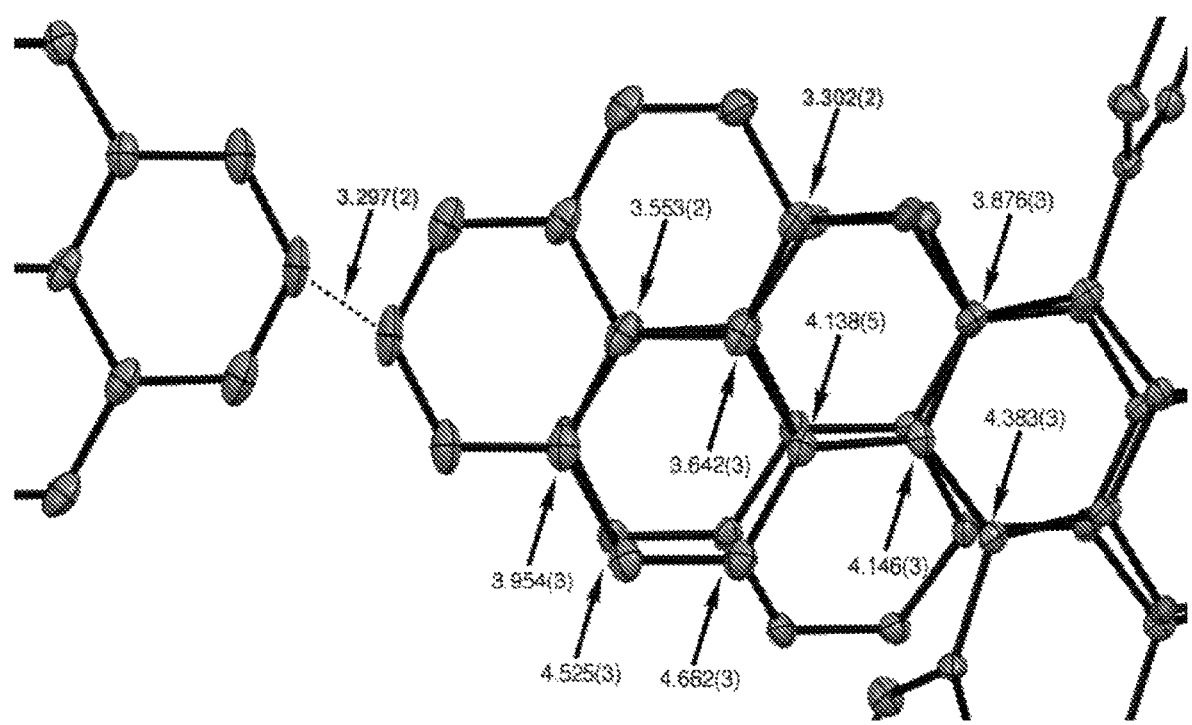
FIG. 8 is the depiction of π-π interactions of compound 7 that occur in a head-to-tail arrangement.

FIG. 8 depicts the π-π interactions of compound 7 that occur in the head-to-tail arrangement. The close C8C6' [3.302(2) Å] and C11'C11' [3.297(2) Å] distances indicate that intermolecular covalent-bonding interactions occur between indicated atoms. Corresponding interatomic distances are in angstroms (Å). Minimal distances are 3.302(2) Å and 3.297(2) Å.

Figure 9:
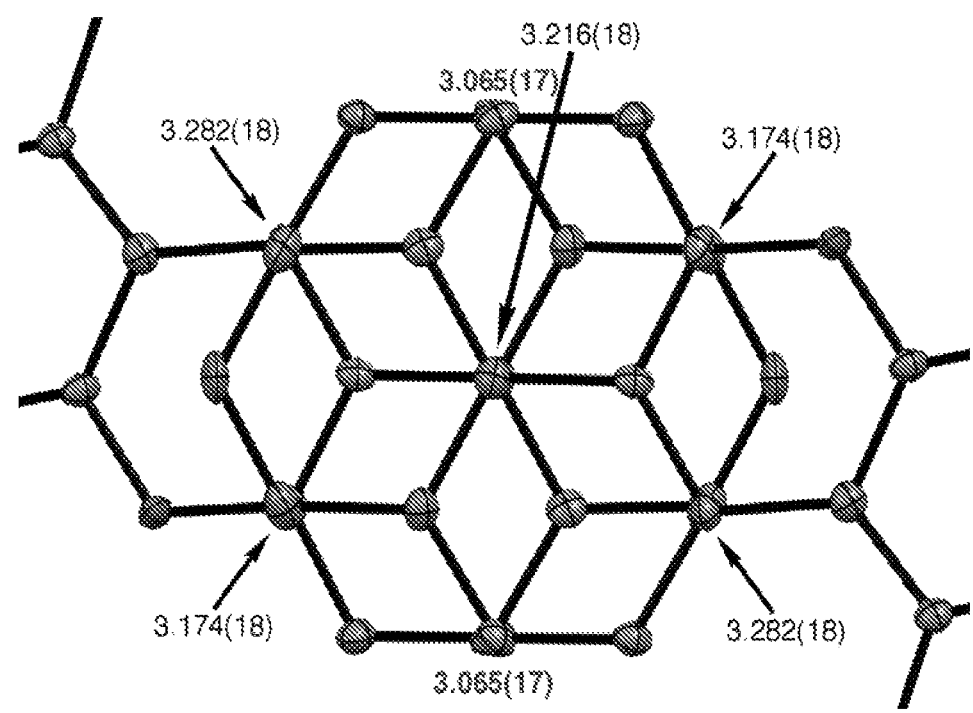
FIG. 9 is a depiction of intermolecular π-π interactions between phenalenyl moieties of compound 7 via head-to-head packing.

FIG. 9 is a depiction of intermolecular π-π interactions between phenalenyl moieties of compound 7 via head-to-head packing. This is an example of "pancake bonding" where overlap of carbons bearing α-spin density is maximized to enable spin-spin coupling. Corresponding interatomic distances are in angstroms (Å), and minimum distances are 3.065(17) seen at the top and bottom.

Figure 10:
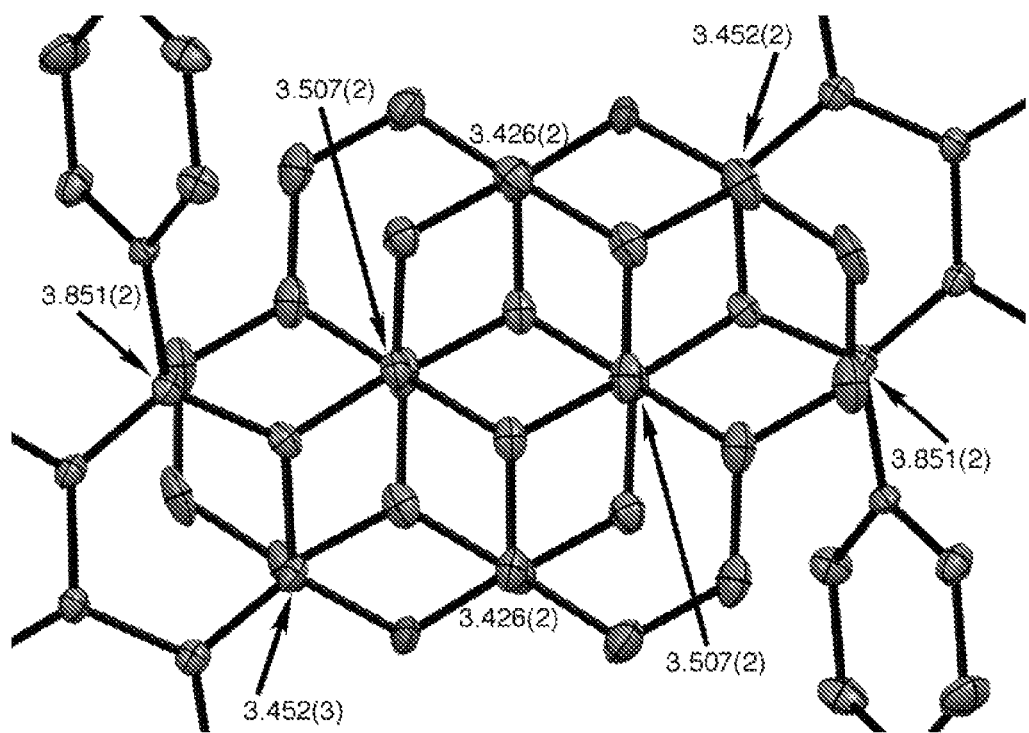
FIG. 10 Depiction of intermolecular π-π interactions between phenalenyl moieties of compound 7 via tail-to-tail packing.

FIG. 10 Depiction of intermolecular π-π interactions between phenalenyl moieties of compound 7 via tail-to-tail packing. Intermolecular covalent-bonding interactions are absent in this π-stacking arrangement that is instead driven by dispersion forces. Corresponding interatomic distances are in angstroms (Å).

Figures 11A, 11B:
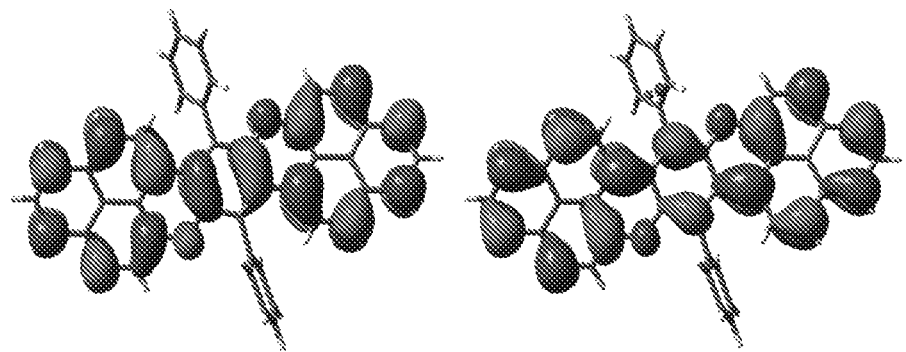
FIGS. 11A-11C depict theoretical calculations for compound 7.
Figure 11C:
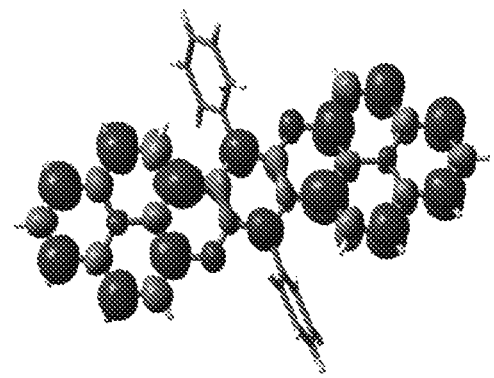
Figure 12:
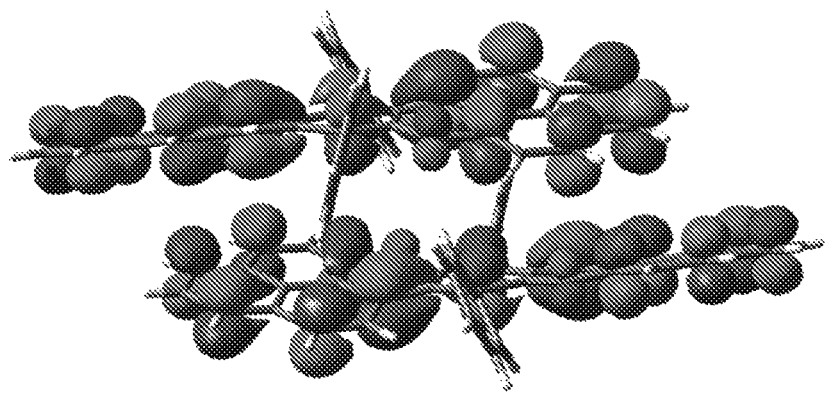
FIG. 12 depicts the calculated LUMO for a dimer that models a head to tail interaction of two compound 7$^+$ molecules.

FIG. 11A-11C depict theoretical calculations for compound 7. Density Functional Theory (DFT) calculations were performed with the Gaussian 09D program on structures with atomic coordinates based on our X-ray crystallographic data. All calculations were carried out using broken symmetry UB3LYP level of theory with a 6-311G (d,p) basis set. Interaction energies were performed using a counterpoise correction calculation. FIG. 11A is the calculated highest occupied molecular orbital (HOMO), FIG. 11B is the lowest unoccupied molecular orbital (LUMO) and FIG. 11C is the calculated spin density for ring atoms (density=0.001 e/au$^3$) of 7$^+$ in the doublet state calculated from B3LYP/6-311G++(d,p). The following is the input data for compound 7$^+$:

p ub3lyp/6-311++g(d,p) scrf=(solvent=chloroform) nosymm guess=save geom=connectivity empiricaldispersion=gd3 pop=full The results of this calculation are:

Total Energy: −1841.492: S**2: 0.75077 FIG. 12 depicts the calculated LUMO for a dimer that models a head to tail interaction of two compound 7$^+$ molecules. Orbital lobes that are close in space have opposite phases and do not display intermolecular overlap. The following is the Counterpoise Calculation for this dimer:

p ub3lyp/6-311g(d,p) nosymm counterpoise=2

Symbolic Z-matrix:

Charge=2 Multiplicity=1 in supermolecule

Charge=1 Multiplicity=2 in fragment 1

Charge=1 Multiplicity=2 in fragment 2

The following are the results obtained:

Counterpoise corrected energy=−3682.627033149625

BSSE energy=0.008337609133 sum of monomers=−3682.713788811555 complexation energy=49.21 kcal/mole (raw)

complexation energy=54.44 kcal/mole (corrected)

Figure 13:
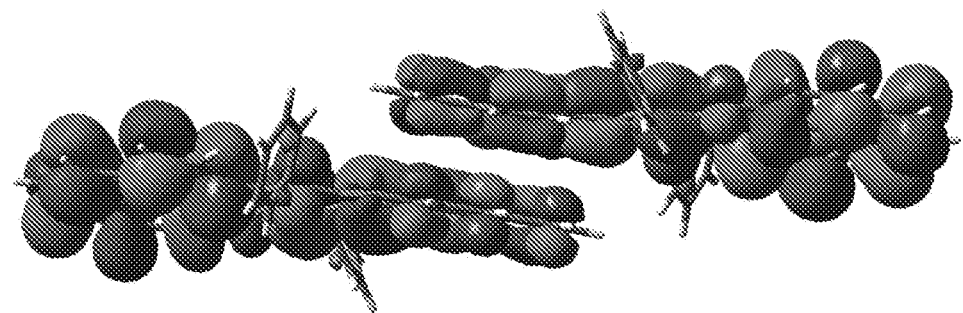
FIG. 13 depicts the calculated LUMO for a dimer that models a head to head interaction of two compound 7$^+$ molecules.

FIG. 13 depicts the calculated LUMO for a dimer that models a head to head interaction of two compound 7$^+$ molecules. Orbital lobes that are close in space have opposite phases and do not display intermolecular overlap. The following is the Counterpoise Calculation for this dimer:

p ub3lyp/6-311g(d,p) nosymm counterpoise=2

Symbolic Z-matrix:

Charge=2 Multiplicity=1 in supermolecule

Charge=1 Multiplicity=2 in fragment 1

Charge=1 Multiplicity=2 in fragment 2

The following are the results obtained:

Counterpoise corrected energy=−3682.652629529630

BSSE energy=0.005678150903 sum of monomers=−3682.713537808238 complexation energy=34.66 kcal/mole (raw)

complexation energy=38.22 kcal/mole (corrected)

Figure 14:
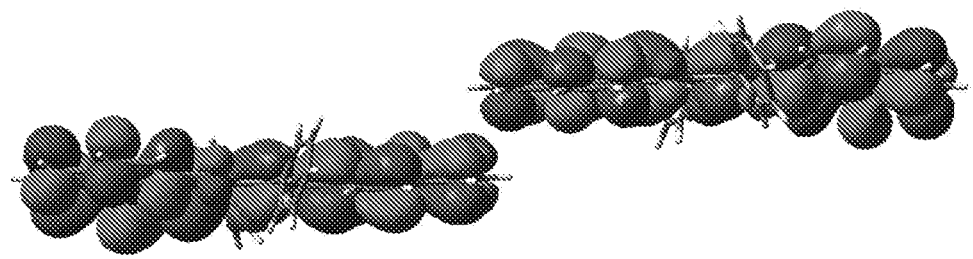
FIG. 14 depicts the calculated LUMO for a dimer that models a tail to tail interaction of two compound 7$^+$ molecules.

FIG. 14 depicts the calculated LUMO for a dimer that models a head to head interaction of two compound 7$^+$ molecules. Orbital lobes that are close in space have opposite phases and do not display intermolecular overlap. The following is the Counterpoise Calculation for this dimer:

p ub3lyp/6-311g(d,p) nosymm counterpoise=2

Symbolic Z-matrix:

Charge=2 Multiplicity=1 in supermolecule

Charge=1 Multiplicity=2 in fragment 1

Charge=1 Multiplicity=2 in fragment 2

The following are the results obtained:

Counterpoise corrected energy=−3682.661737615167

BSSE energy=0.000957309562 sum of monomers=−3682.713557501942 complexation energy=31.92 kcal/mole (raw)

complexation energy=32.52 kcal/mole (corrected)

Figure 15:
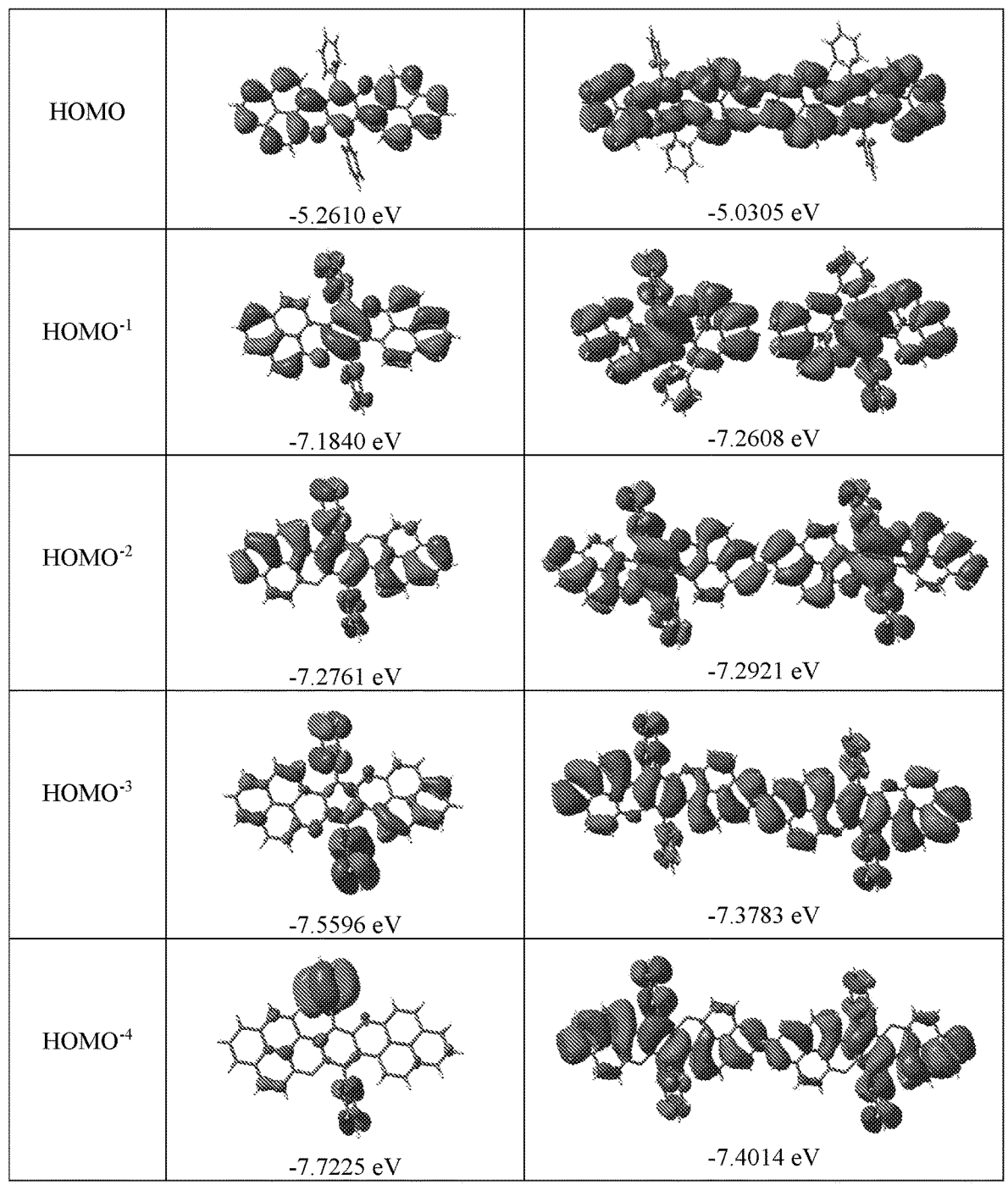
FIG. 15 depicts of the five highest occupied MOs for the single compound 7$^+$ unit and the dimer that models the tail-to-tail arrangement.

FIG. 15 depicts of the five highest occupied MOs for the single compound 7$^+$ unit and the dimer that models the tail-to-tail arrangement.

Figure 16:
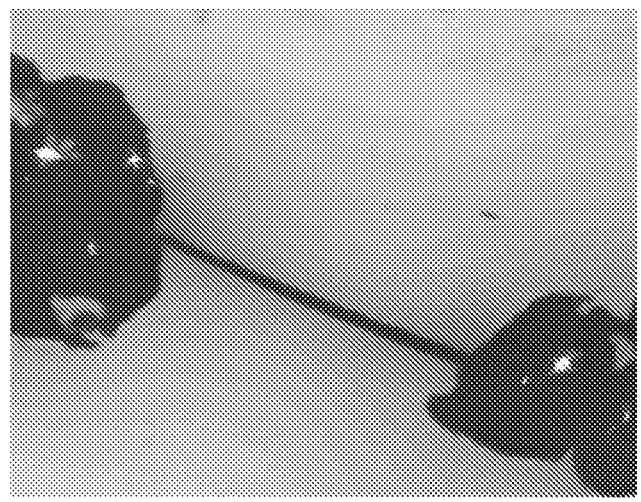
FIG. 16 depicts a single crystal device comprising compound 7.
Figure 17A:
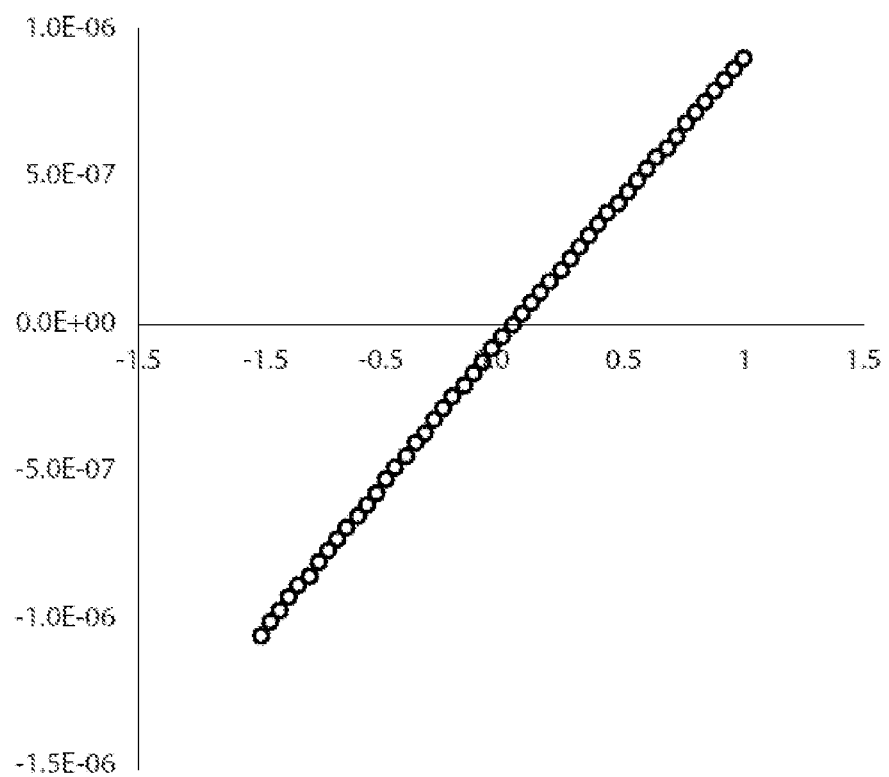
FIGS. 17A-17C depict current-voltage curves for 3 separate devices comprising compound 7 as measured by a two point probe method.
Figure 17B:
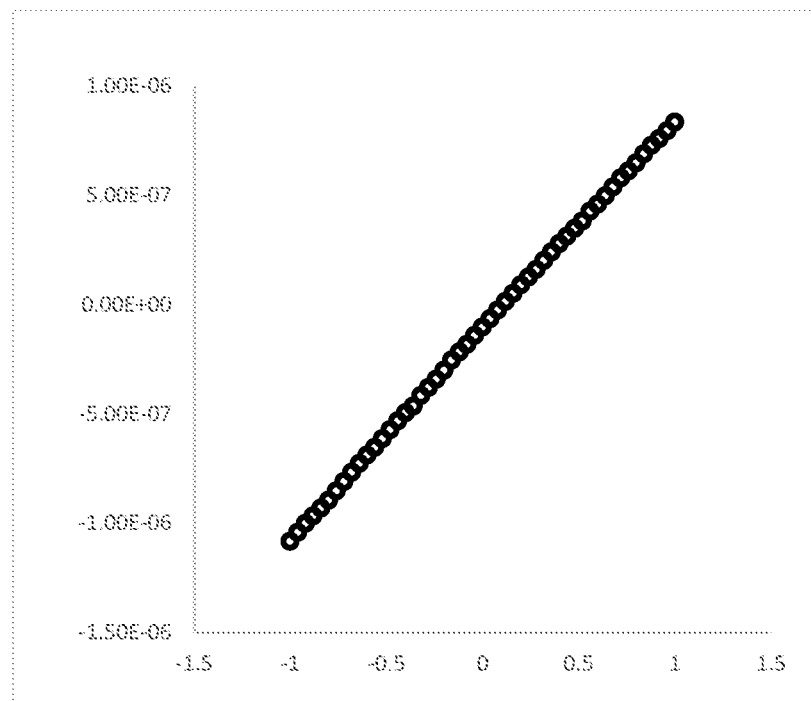
Figure 17C:
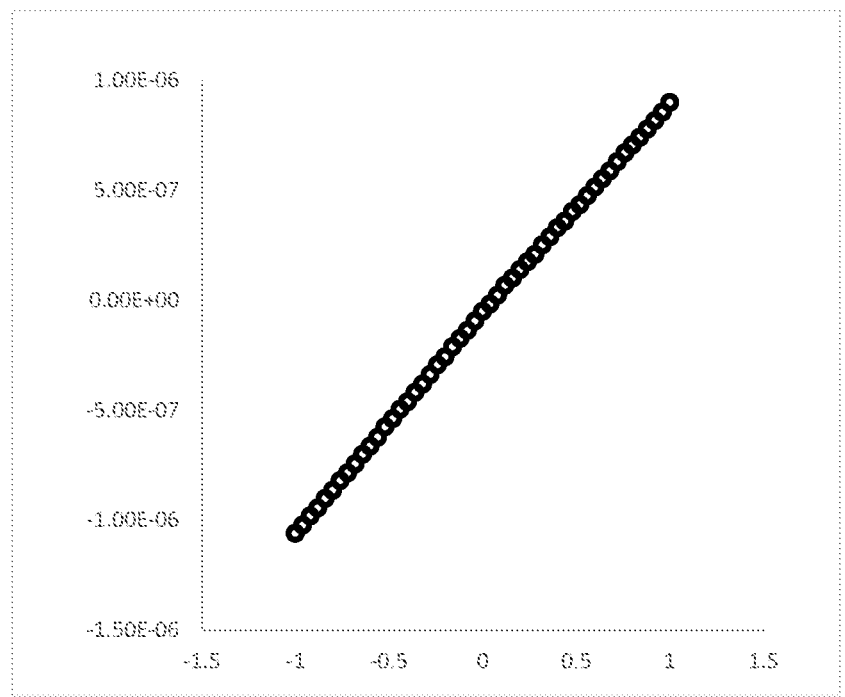

FIG. 16 depicts a single crystal device comprising compound 7 where a single crystal needle is mounted to a glass slide and graphite paste is applied to both ends of the crystal. Conductivity measurements were performed using the two probe method on a Keithley 4200 SCS with a Signatone 1160 probe station on single crystals of compound 7. The crystals were grown by solvent diffusion of diethyl ether into a solution of compound 7 in TCE. Crystals were then mounted on a clean glass slide and graphite paste (Electron Microscopy Sciences, graphite conductive adhesive 112) was applied to both ends of the crystals. Crystal dimensions were determined through a calibrated optical microscope to determine the width of the conduction channel. The slides were then placed on the probe station chuck, and tungsten probes mounted on micromanipulators (5 μm resolution) were lowed to contact the graphite paste to perform the measurements. I-V curves were performed between −1 V to 1V in a glovebox at room temperature with 0% humidity in the dark. Due to instrument limitations a 1 MΩ resistor was placed in series to acquire the data. The value of the resistor was determined to be 976334.3Ω, and this value was used to back-calculate the resistance of compound 7. Using the adjusted resistance, conductivity values were calculated using the equation below where L is the length of conduction channel w is the width and t is the thickness, all of which are in centimeters (cm). The following formula is used to provide the data in Table 1

$$\sigma = \frac{I}{V}\frac{L}{wt}$$

TABLE 1

| Device | Resistance (kΩ) | L (cm) | w (cm) | t (cm) | Conductivity (S/cm) |
|---|---|---|---|---|---|
| 16A | 50.8 | 0.0315 | 0.0080 | 0.0080 | 0.0097 |
| 16B | 45.1 | 0.0300 | 0.0060 | 0.0060 | 0.0184 |
| 16C | 64.2 | 0.0222 | 0.0055 | 0.0055 | 0.0114 |

Figure 18:
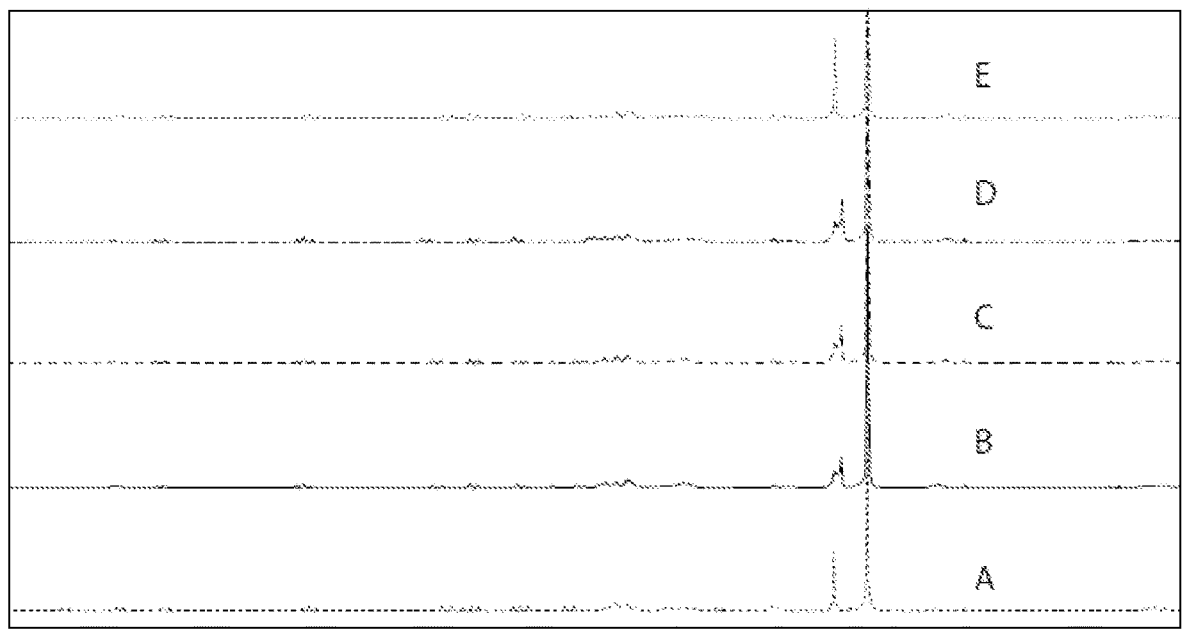
FIG. 18 is a series of Evans method proton VT-NMR data of compound 7 in $CDCl_3$ and TCE.

FIG. 18 is a series of Evans method proton VT-NMR data of compound 7 in $CDCl_3$ and TCE. In solution NMR, reversible changes to magnetic susceptibility were observed in a range between 243-303 K. At 298 K, the magnetic moment ($\mu_{eff}$) was measured to be $0.735\mu_B$ (0.252 e⁻ per molecule). When brought to 243 K, $\mu_{eff}$ decreased to $0.591\mu_B$ (0.161 e⁻ per molecule). Upon warming to 303K, the magnetic moment increased to $0.759\mu_B$ (0.255 e⁻ per molecule). Spectra were taken at fifteen minute intervals in order to let samples equilibrate. The initial spectra (A) was taken at 298K and then cooled to 273K (B), 253K (C), and 243K (D). The sample was warmed to 303K (D) to show reversibility.

Figure 19:
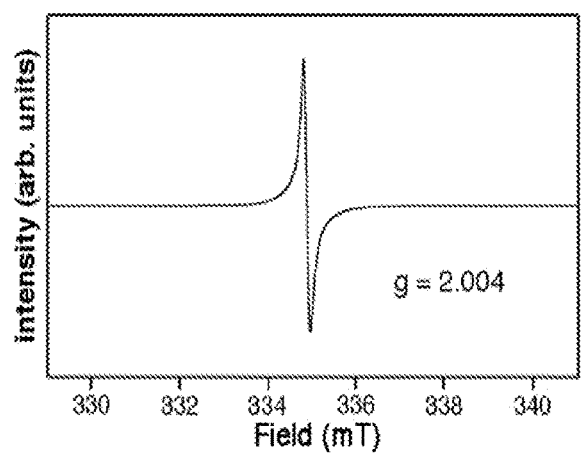
FIG. 19 depicts the electron paramagnetic resonance of compound 7.

FIG. 19 depicts the electron paramagnetic resonance of compound 7 taken at 11K as a solid diluted in high purity silica. The sample was prepared for EPR analysis in a glovebox under inert atmosphere (N2) for EPR analysis by diluting solid compound 7 in high purity silica. The dilute EPR sample was contained in a 4 mm OD Suprasil quartz EPR tube (Wilmad Labglass). The X-band EPR spectrum was recorded at 11K on a Bruker EMXplus spectrometer equipped with a 4119HS cavity and an Oxford ESR-900 helium flow cryostat.

Table 2 provides the spectral parameters of the EPR spectrum.

TABLE 2

| | |
|---|---|
| Center Field, G | 3359.8 |
| Sweep Width, G | 200.0 |
| Sweep Time, s | 200.0 |
| Receiver Gain, dB | 30 |
| Modulation Amplitude, G | 1.000 |
| Attenuation, dB | 20.0 |
| Modulation Frequency, kHz | 100.00 |
| Power, mW | 2.000 |
| Conversion Time, ms | 100.0 |
| Time Constant, ms | 0.01 |
| Temperature, K | 11 |
| Frequency, GHz | 9.39 |

Compound Film Deposition

Glass slides (10×10 mm) are cleaned by sonication in a 2% solution of Hellmanex detergent in water (15 min), deionized water (15 min), acetone (15 min), and isopropanol (15 min), and are then dried under a stream of N2. Compound 6 (5 mg/mL-25 mg/mL) and poly(styrenesulfonate) sodium salt (PSS) (wt % 10-500) are suspended in 3M sulfuric acid solution (0.1 mL) using deionized water, and stirred for 100° C. for 24 h. Spin coating is performed by slowly dropping the compound 6/ploymer solution on to a clean glass slide that is spinning at 2500 rpm. The glass slide is allowed to spin for 2 minutes to facilitate drying of the thin film. Indium (In) wire (0.5 mm diameter) is cut into disks and pressed onto the four corners of the glass slide in order to be used as electrodes. Using the four electrode contacts, current-voltage (I-V) characteristics and Hall effect measurements are performed to quantify the mobility, charge carrier type, and resistance of the films on an ECOPIA HMS-5500 Hall Effect measurement system. Conductivities were calculated with the measurement of thin film thicknesses, which were determined by atomic force microscope analysis with a Bruker/VEECO DI-3000.

FIG. 19 depicts a film made by this process. The film thickness if from 20 nm to 90 nm. The conductivity (GRT) was 0.03-0.12 S/cm using the Van der Pauw method.

Figure 20:
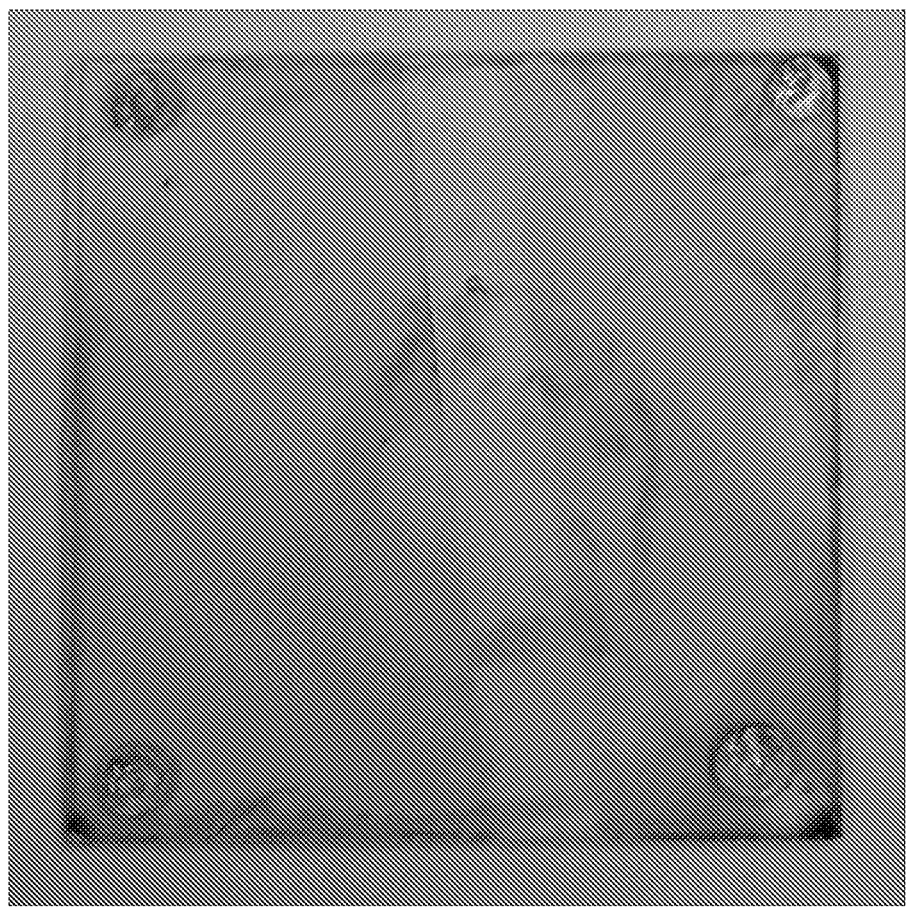
FIG. 20 depicts a spin coated film of compound 6/poly (styrenesulfonate) sodium salt film.

FIG. 20 depicts a spin coated film of compound 6/poly (styrenesulfonate) sodium salt film.

Process

Disclosed herein are processes for preparing the disclosed compounds. In a first aspect the process relates to preparing compounds having the formula:

i)

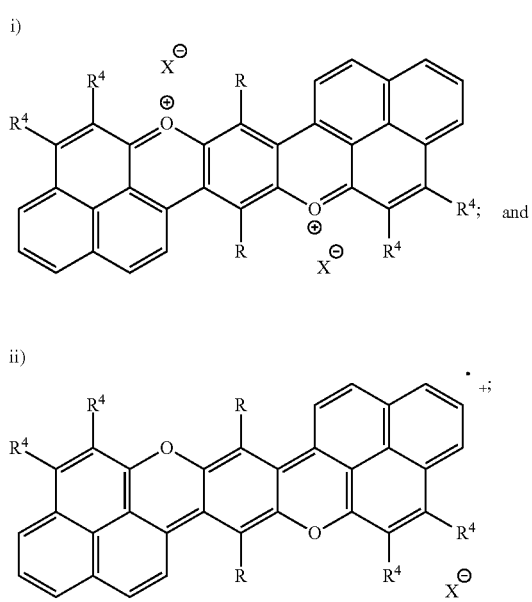

comprising:

A) treating a compound having the formula:

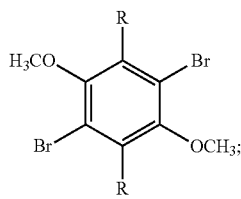

R is chosen from substituted or unsubstituted phenyl, said substitutions are independently chosen from:

i) $OR^1$, $R^1$ chosen from hydrogen, substituted or unsubstituted $C_1$-$C_4$ linear, branched or cyclic alkyl, substituted or unsubstituted phenyl, said substitutions chosen from hydroxyl, $C_1$-$C_4$ linear, branched or cyclic alkyl, or mixtures thereof;

ii) $NR^2R^2$, each $R^2$ is independently chosen from hydrogen, $C_1$-$C_4$ linear, branched or cyclic alkyl, or mixtures thereof;

iii) substituted or unsubstituted $C_1$-$C_6$ linear, branched or cyclic alkyl, said substitutions chosen from hydroxyl, $C_1$-$C_4$ linear, branched or cyclic alkyl, phenyl, or mixtures thereof, iv) substituted or unsubstituted aryl chosen from phenyl, naphthyl, phenathrenyl, fluorenyl, of mixtures thereof,
v) substituted or unsubstituted heteroaryl;
with a strong base to form an intermediate; reacting the intermediate with a compound having the formula:

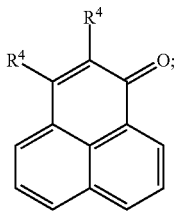

in the presence of an oxidizing agent, wherein each $R^4$ is independently chosen from:
i) $OR^5$, $R^5$ chosen from hydrogen, substituted or unsubstituted $C_1$-$C_4$ linear, branched or cyclic alkyl, substituted or unsubstituted phenyl, said substitutions chosen from hydroxyl, $C_1$-$C_4$ linear, branched or cyclic alkyl, or mixtures thereof;
ii) $NR^6R^6$, each $R^6$ is independently chosen from hydrogen, $C_1$-$C_4$ linear, branched or cyclic alkyl, or mixtures thereof;
iii) substituted or unsubstituted $C_1$-$C_6$ linear, branched or cyclic alkyl, said substitutions chosen from hydroxyl, $C_1$-$C_4$ linear, branched or cyclic alkyl, phenyl, or mixtures thereof, or
iv) a polyethylene glycol unit having the formula:

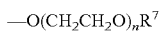

$R^7$ is hydrogen or $C_1$-$C_4$ alkyl, the index n is from about 5 to about 500;
to form a compound having the formula:

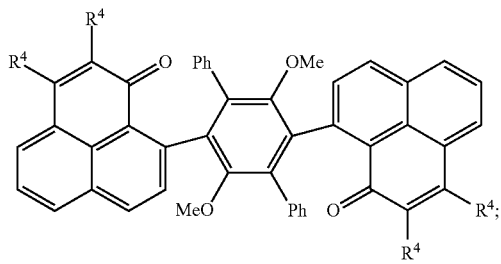

B) reacting the compound formed in step (A) with a strong acid to form a compound having the formula:

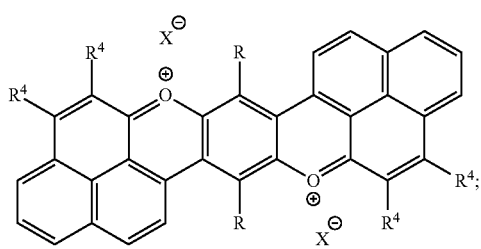

wherein X is a counter ion formed from the strong acid, Y is O or N; or

C) optionally reacting the compound formed in step (B) with a reducing agent to form a compound having the formula:

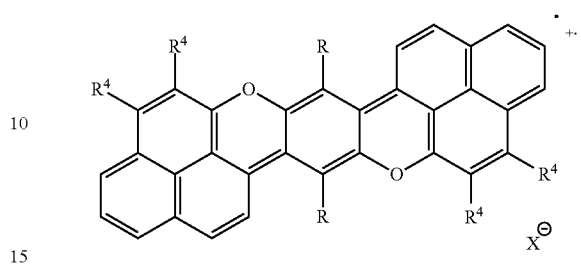

Further disclose herein are processes for preparing the disclosed compounds. In a first aspect the process relates to preparing compounds having the formula:

i)

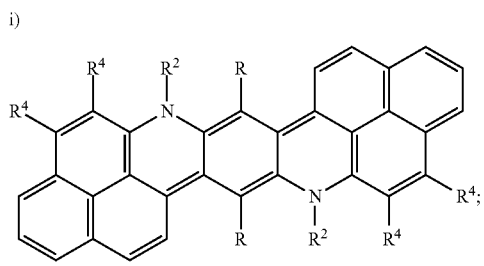

ii)

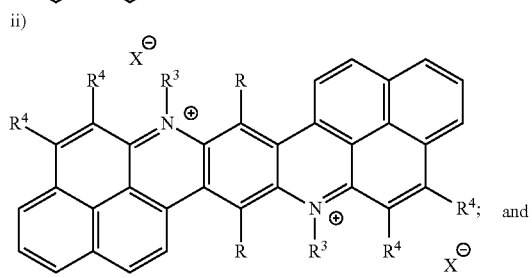

iii)

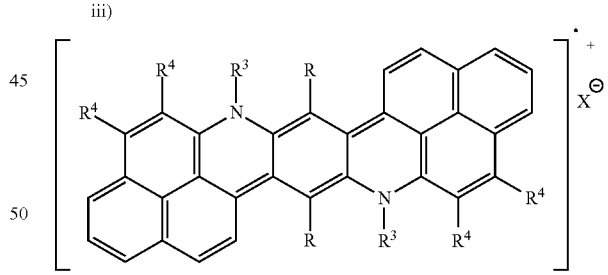

comprising:
A) treating a compound having the formula:

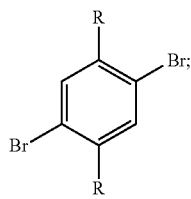

R is chosen from substituted or unsubstituted phenyl, said substitutions are independently chosen from:
i) OR$^1$, R$^1$ chosen from hydrogen, substituted or unsubstituted C$_1$-C$_4$ linear, branched or cyclic alkyl, substituted or unsubstituted phenyl, said substitutions chosen from hydroxyl, C$_1$-C$_4$ linear, branched or cyclic alkyl, or mixtures thereof;
ii) NR$^2$R$^2$, each R$^2$ is independently chosen from hydrogen, C$_1$-C$_4$ linear, branched or cyclic alkyl, or mixtures thereof;
iii) substituted or unsubstituted C$_1$-C$_6$ linear, branched or cyclic alkyl, said substitutions chosen from hydroxyl, C$_1$-C$_4$ linear, branched or cyclic alkyl, phenyl, or mixtures thereof,
iv) substituted or unsubstituted aryl chosen from phenyl, naphthyl, phenathrenyl, fluorenyl, of mixtures thereof,
v) substituted or unsubstituted heteroaryl;
with a strong base to form an intermediate; reacting the intermediate with a compound having the formula:

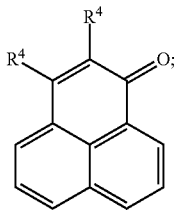

in the presence of an oxidizing agent, wherein each R$^4$ is independently chosen from:
i) OR$^5$, R$^5$ chosen from hydrogen, substituted or unsubstituted C$_1$-C$_4$ linear, branched or cyclic alkyl, substituted or unsubstituted phenyl, said substitutions chosen from hydroxyl, C$_1$-C$_4$ linear, branched or cyclic alkyl, or mixtures thereof;
ii) NR$^6$R$^6$, each R$^6$ is independently chosen from hydrogen, C$_1$-C$_4$ linear, branched or cyclic alkyl, or mixtures thereof;
iii) substituted or unsubstituted C$_1$-C$_6$ linear, branched or cyclic alkyl, said substitutions chosen from hydroxyl, C$_1$-C$_4$ linear, branched or cyclic alkyl, phenyl, or mixtures thereof, or
iv) a polyethylene glycol unit having the formula:

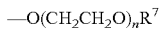

—O(CH$_2$CH$_2$O)$_n$R$^7$

R$^7$ is hydrogen or C$_1$-C$_4$ alkyl, the index n is from about 5 to about 500;
to form a compound having the formula:

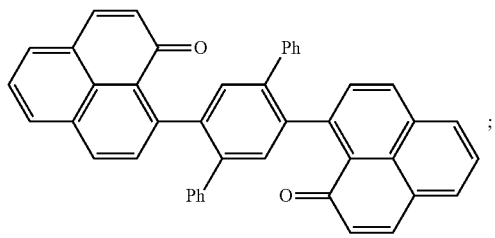 [SMILES: O=C1C=Cc2cccc3ccc(-c4cc(-c5ccccc5)c(-c5ccc6cccc7c6c5C(=O)C=C7)cc4-c4ccccc4)c1c23]

B) reacting the compound formed in step (A) with hydroxyl amine and an acylating agent to form a compound having the formula:

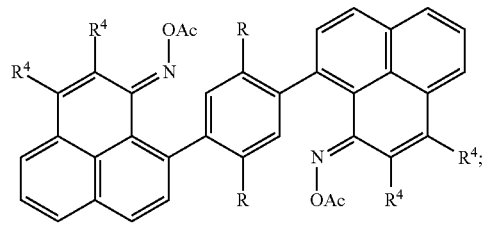

C) reacting the compound formed in step (B) with a Fe(III) catalyst to form a compound having the formula:

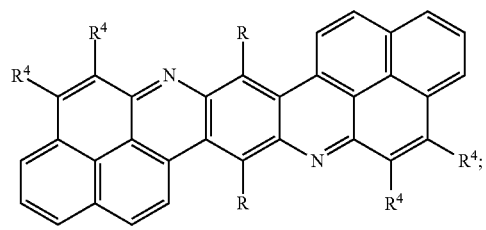

D) reacting the compound formed in step (C) with methyl trifluoromethane sulphonate to form a compound having the formula:

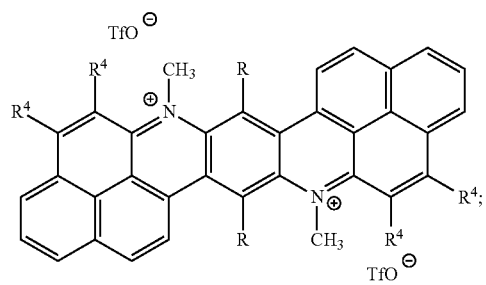

E) reacting the compound formed in Step (D) with a reducing reagent to form the compound having the formula:

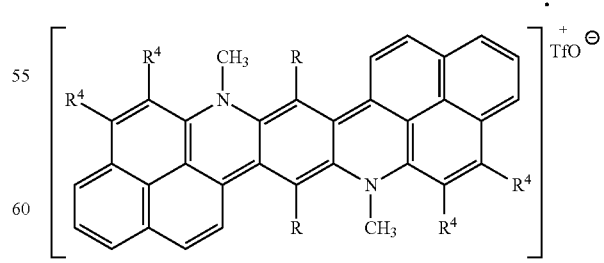

In one embodiment of this process acetic anhydride is used as the acylating agent in step (B). In one embodiment of this process Fe(acac) is used as the ring closure catalyst in step (C).

The disclosed compounds are useful in organic molecule electron transport devices; p- (electron) versus n- (hole) transport. The disclosed compounds can be layered head to tail as seen in FIG. 12, layered head to head as depicted in FIG. 13 or the compounds can be layered tail to tail as depicted in FIG. 14 depending upon the type of electronic characterization and current transfer efficiency desired by the formulator. In addition, the formulator can use a mixture of these alignments to obtain the efficiency desired.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A compound having the formula:

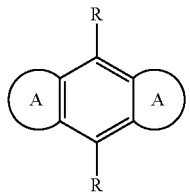

wherein R is chosen from substituted or unsubstituted phenyl, said substitutions are independently chosen from:
i) $OR^1$, wherein $R^1$ is selected from hydrogen, substituted or unsubstituted $C_1$-$C_{18}$ linear, branched or cyclic alkyl, and substituted or unsubstituted phenyl, said substitutions are selected from hydroxyl, $C_1$-$C_{18}$ linear, branched or cyclic alkyl, and combinations thereof;
ii) $NR^2R^2$, wherein each $R^2$ is independently selected from hydrogen and $C_1$-$C_4$ linear, branched or cyclic alkyl;
iii) substituted or unsubstituted $C_1$-$C_{18}$ linear, branched or cyclic alkyl, said substitutions are selected from hydroxyl, $C_1$-$C_8$ linear, branched or cyclic alkyl, phenyl, and combinations thereof;
iv) substituted or unsubstituted aryl chosen from phenyl, naphthyl, phenanthrenyl, or fluorenyl; and
v) substituted or unsubstituted heteroaryl;

wherein A has the formula chosen from:

i)

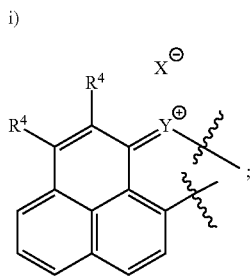

ii)

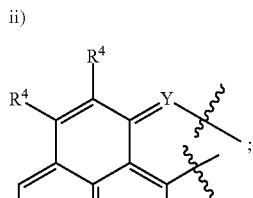

iii)

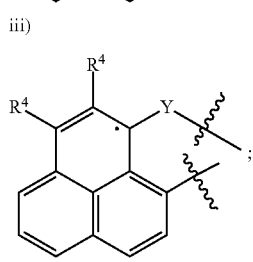

iv) combinations thereof;

each $R^4$ is independently chosen from:
i) $OR^5$, wherein $R^5$ is selected from hydrogen, substituted or unsubstituted $C_1$-$C_{18}$ linear, branched or cyclic alkyl, and substituted or unsubstituted phenyl, said substitutions are selected from hydroxyl, $C_1$-$C_4$ linear, branched or cyclic alkyl, and combinations thereof;
ii) $NR^6R^6$, wherein each $R^6$ is independently chosen from hydrogen, $C_1$-$C_4$ linear, branched or cyclic alkyl;
iii) hydrogen, substituted or unsubstituted $C_1$-$C_{18}$ linear, branched or cyclic alkyl, said substitutions are selected from hydroxyl, $C_1$-$C_4$ linear, branched or cyclic alkyl, phenyl, and combinations thereof; or
iv) a polyethylene glycol unit having the formula:

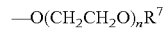
—O(CH$_2$CH$_2$O)$_n$R$^7$ $R^7$ is hydrogen or $C_1$-$C_4$ alkyl, the index n is from about 5 to about 500;

each Y is independently chosen from O, N, S, P, SO, SO$_2$, PO, NO, NR$^3$, or C(R$^8$)$_2$; each $R^8$ is independently chosen from:
i) $OR^9$, wherein $R^9$ is chosen from hydrogen, substituted or unsubstituted $C_1$-$C_4$ linear, branched or cyclic alkyl, and substituted or unsubstituted phenyl, said substitutions are chosen from hydroxyl, $C_1$-$C_4$ linear, branched or cyclic alkyl, and combinations thereof;
ii) $NR^{10}R^{10}$, wherein each $R^{10}$ is independently selected from hydrogen and $C_1$-$C_4$ linear, branched or cyclic alkyl; or
iii) substituted or unsubstituted $C_1$-$C_6$ linear, branched or cyclic alkyl, said substitutions are chosen from hydroxyl, $C_1$-$C_4$ linear, branched or cyclic alkyl, phenyl, and combinations thereof; and each X is an anion independently chosen from halogen, BF$_4^-$, ClO$_4^-$, triflate, mesylate, tosylate, and combinations thereof.

2. The compound according to claim 1, wherein $R^4$ is hydrogen, hydroxyl, $C_1$-$C_3$ linear or branched alkyl, or $C_1$-$C_3$ linear or branched alkoxy.

3. The compound according to claim 1, wherein A has the formula:
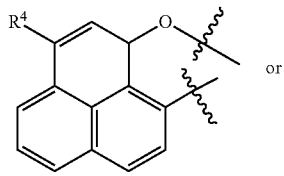 or
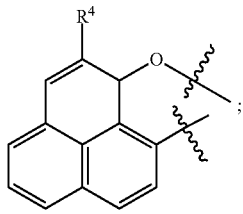 ;
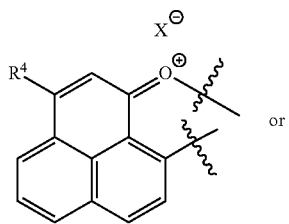 or
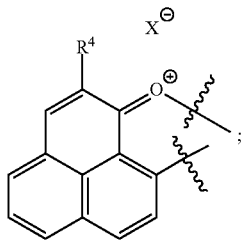 ;
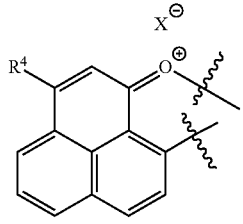 and
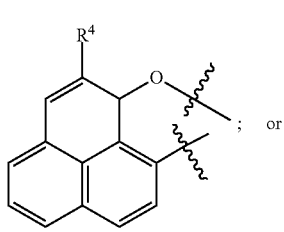 ; or
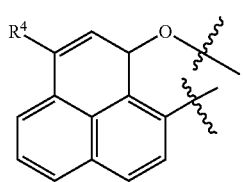 and
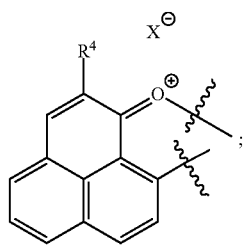 ;
wherein $R^4$ is independently selected from hydrogen, hydroxyl, and $C_1$-$C_3$ linear or branched alkyl, $C_1$-$C_3$ linear or branched alkoxy.
4. The compound according to claim 1, wherein A has the formula:
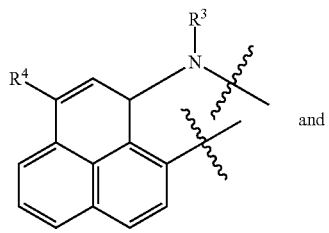 and
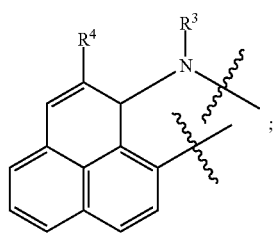 ;
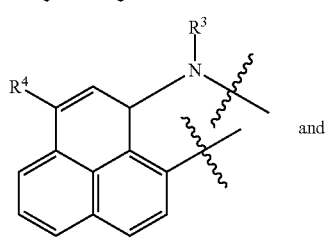 and
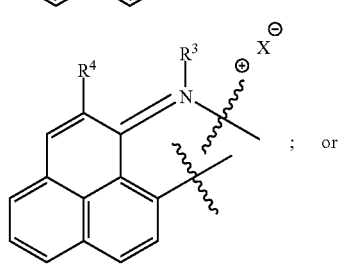 ; or
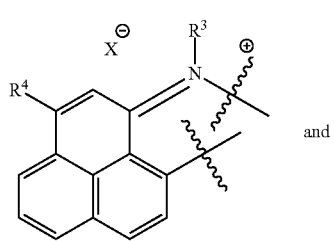 and -continued

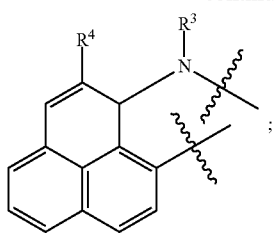

wherein each R³ is independently selected from hydrogen and substituted or unsubstituted $C_1$-$C_4$ linear, branched or cyclic alkyl; R⁴ units is hydrogen, hydroxyl, or $C_1$-$C_3$ linear or branched alkyl, $C_1$-$C_3$ linear or branched alkoxy.

5. The compound according to claim 1, wherein R⁴ is hydrogen, methyl, ethyl, propyl, isopropyl, methoxy, ethoxy, propoxy, or isopropoxy.

6. The compound according to claim 1, wherein R⁴ is hydrogen.

7. A compound having a formula selected from:

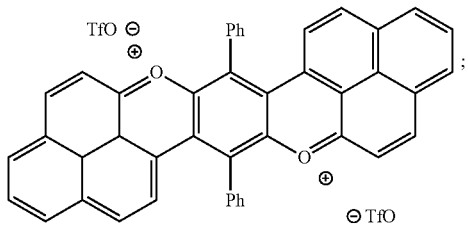

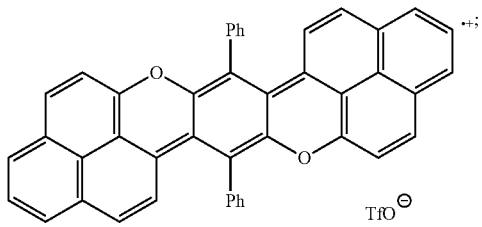

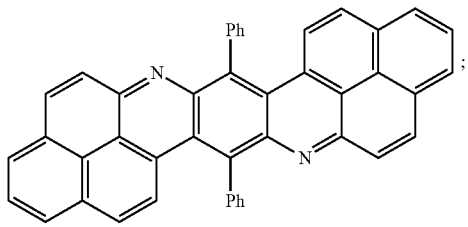

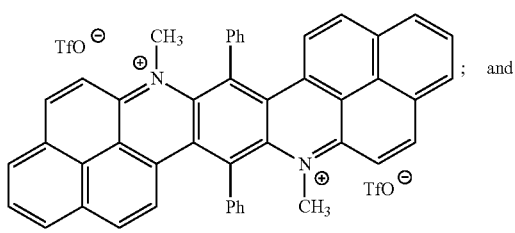

and

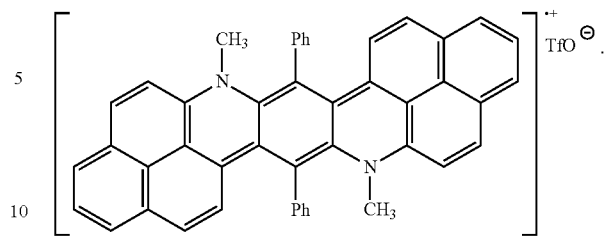

8. A process for preparing a compound according to claim 1, the compound having the formula:

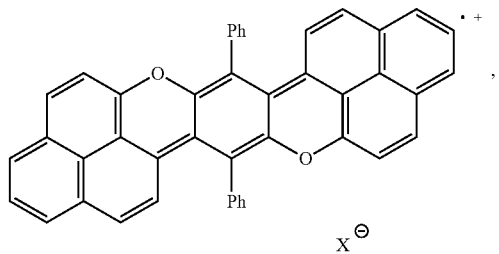

the process comprising:

A) treating a compound having the formula:

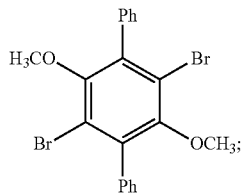 [SMILES: COc1c(Br)c(-c2ccccc2)c(OC)c(Br)c1-c1ccccc1]

with a strong base to form an intermediate in situ; reacting the intermediate with 1H-phenalen-1-one having the formula:

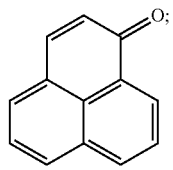 [SMILES: O=C1C=Cc2cccc3cccc1c23]

to form a compound having the formula:

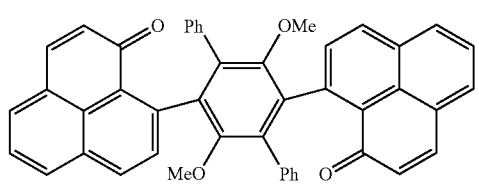 [SMILES: COc1c(-c2ccccc2)c(-c2ccc3cccc4c3c2C(=O)C=C4)c(OC)c(-c2ccccc2)c1-c1ccc2cccc3c2c1C(=O)C=C3]

B) reacting the compound formed in step (A) with a strong acid to form a compound having the formula:

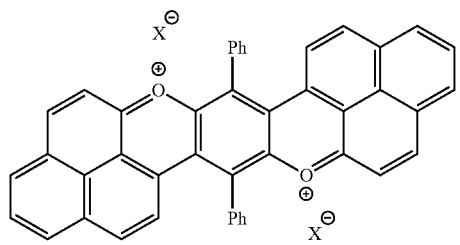

wherein X is the anion of a strong acid;

C) reacting the compound formed in step (B) with a reducing agent to form a compound having the formula:

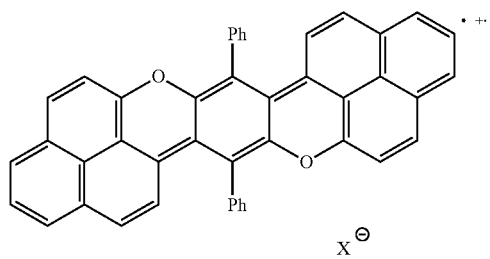

9. The process according to claim 8, wherein the strong acid is trifluoromethanesulfonic acid.

10. The process according to claim 8, wherein the reducing agent is sodium dithionate, $Na_2S_2O_4$.

11. A process for preparing a compound according to claim 7, having the formula:

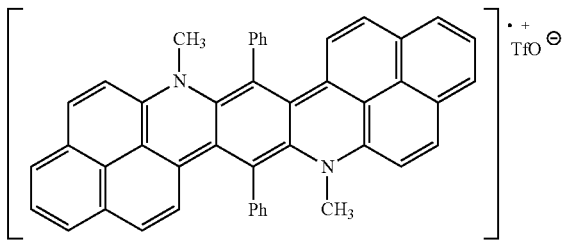

A) treating a compound having the formula:

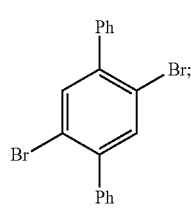 [SMILES: Brc1cc(-c2ccccc2)c(Br)cc1-c1ccccc1]

with a strong base to form an intermediate in situ; reacting the intermediate with 1H-phenalen-1-one having the formula:

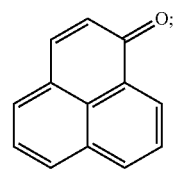 [SMILES: O=C1C=Cc2cccc3cccc1c23]

to form a compound having the formula:

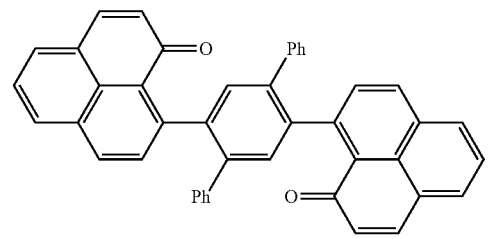 [SMILES: O=C1C=Cc2cccc3ccc(-c4cc(-c5ccccc5)c(-c5ccc6cccc7c6c5C(=O)C=C7)cc4-c4ccccc4)c1c23]

B) reacting the compound formed in (A) with hydroxyl amine and acetic anhydride to form a compound having the formula:

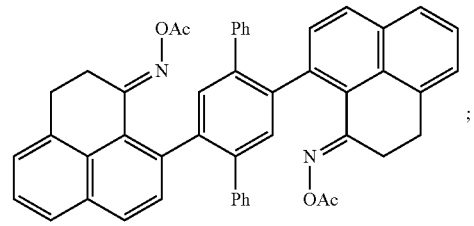 [SMILES: CC(=O)O/N=C1\CCc2cccc3ccc(-c4cc(-c5ccccc5)c(-c5ccc6cccc7c6c5/C(=N/OC(C)=O)CC7)cc4-c4ccccc4)c1c23]

C) reacting the compound formed in step (B) with a Fe(III) catalyst to form a compound having the formula:

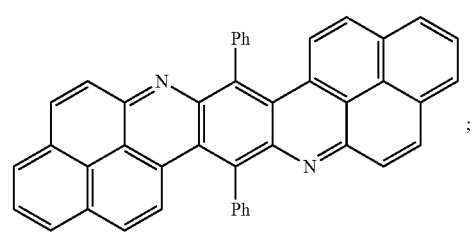 [SMILES: c1ccc(-c2c3nc4ccc5cccc6ccc(c3c(-c3ccccc3)c3nc7ccc8cccc9ccc(c23)c7c89)c4c56)cc1]

D) reacting the compound formed in step (C) with methyl trifluoromethane sulphonate to form a compound having the formula:
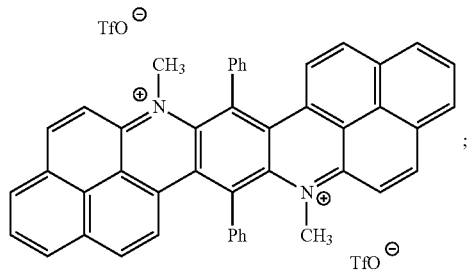 [SMILES: C[n+]1c2ccc3cccc4ccc(c5c(-c6ccccc6)c6c(c(-c7ccccc7)c51)c1ccc5cccc7ccc(c1c57)[n+]6C)c2c43]
E) reacting the compound formed in Step (D) with a reducing reagent to form the compound having the formula:
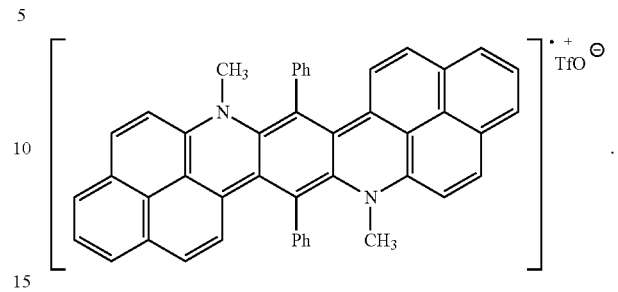
12. The process according to claim 11, where in the iron catalyst is Fe(acac)$_3$.
* * * * *